(12) United States Patent
Schulte et al.

(10) Patent No.: US 9,138,210 B2
(45) Date of Patent: Sep. 22, 2015

(54) FISTULA CLEANING AND REPAIR DEVICE AND METHOD

(75) Inventors: John B. Schulte, West Chester, OH (US); Rebecca J. Mollere, Loveland, OH (US); Patrick D. Dugan, Madeira, OH (US); Michael D. Cronin, Cincinnati, OH (US); Jerome R. Morgan, Cincinnati, OH (US); Joanne Hull, Cincinnati, OH (US); Wells D. Haberstich, Loveland, OH (US); James A. Woodard, Jr., Mason, OH (US); Peter K. Shires, Hamilton, OH (US); Barbara L. Mattson, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 782 days.

(21) Appl. No.: 12/777,697

(22) Filed: May 11, 2010

(65) Prior Publication Data
US 2011/0282354 A1    Nov. 17, 2011

(51) Int. Cl.
*A61B 17/22*    (2006.01)
*A61B 17/00*    (2006.01)
(Continued)

(52) U.S. Cl.
CPC ....... *A61B 17/0057* (2013.01); *A61B 17/12099* (2013.01); *A61B 17/12168* (2013.01); *A61B 17/32075* (2013.01);
(Continued)

(58) Field of Classification Search
CPC ..................... A61B 17/0057; A61B 17/12099; A61B 17/32075; A61B 17/00641; A61B 2017/00942; A61B 2017/00623

USPC ............... 604/1–3, 11–18, 22, 46–47, 93.01, 604/890.1, 892.1; 606/213–217, 151–153, 606/159, 191–199, 232, 108, 127, 128, 606/110–115; 623/1.11–1.54
See application file for complete search history.

(56) References Cited

U.S. PATENT DOCUMENTS

| | | | |
|---|---|---|---|
| 5,312,427 A * | 5/1994 | Shturman | ..................... 606/159 |
| 5,526,822 A | 6/1996 | Burbank et al. | |
| 5,694,951 A | 12/1997 | Bonutti | |

(Continued)

FOREIGN PATENT DOCUMENTS

WO        WO 96/33658        10/1996

OTHER PUBLICATIONS

International Search Report and Written Opinion dated Sep. 9, 2011 for Application No. PCT/US2011/035905.

(Continued)

*Primary Examiner* — Ryan Severson
*Assistant Examiner* — Rachel S Papeika
(74) *Attorney, Agent, or Firm* — Frost Brown Todd LLC

(57) ABSTRACT

A fistula cleaning and repairing device comprises a device for cleaning a fistula and a device for repairing a fistula. Some versions of the device for cleaning a fistula comprise a rotary device with ah head configured to debride a fistula. Some versions of the device for cleaning comprise an abrasive catheter. Some versions of the device for cleaning comprise a plurality of abrasive beads. Some versions of the device for repairing a fistula comprise an implantable stent. Some versions of the device for repairing a fistula comprise an implantable mesh. Some versions of the device for repairing a fistula comprise a swab configured to deliver a medical fluid.

15 Claims, 21 Drawing Sheets

(51) Int. Cl.
*A61B 17/12* (2006.01)
*A61B 17/3207* (2006.01)

(52) U.S. Cl.
CPC .............. *A61B 2017/00623* (2013.01); *A61B 2017/00641* (2013.01); *A61B 2017/00942* (2013.01)

(56) References Cited

U.S. PATENT DOCUMENTS

| | | | |
|---|---|---|---|
| 5,947,985 A * | 9/1999 | Imran | 606/159 |
| 6,086,544 A | 7/2000 | Hibner et al. | |
| 6,203,563 B1 * | 3/2001 | Fernandez | 606/215 |
| 6,990,982 B1 | 1/2006 | Bonutti | |
| 7,115,100 B2 | 10/2006 | McRury et al. | |
| 7,442,171 B2 | 10/2008 | Stephens et al. | |
| 7,611,473 B2 | 11/2009 | Boock et al. | |
| 2004/0078090 A1 | 4/2004 | Binette et al. | |
| 2004/0193071 A1 | 9/2004 | Binette et al. | |
| 2005/0038520 A1 | 2/2005 | Binette et al. | |
| 2005/0113736 A1 | 5/2005 | Orr et al. | |
| 2005/0125077 A1 | 6/2005 | Harmon et al. | |
| 2006/0024357 A1 * | 2/2006 | Carpenter et al. | 424/445 |
| 2007/0198059 A1 * | 8/2007 | Patel et al. | 606/213 |
| 2007/0208134 A1 * | 9/2007 | Hunter et al. | 525/54.1 |
| 2008/0071385 A1 | 3/2008 | Binette et al. | |
| 2008/0214955 A1 | 9/2008 | Speeg et al. | |
| 2008/0228171 A1 * | 9/2008 | Kugler et al. | 604/529 |
| 2008/0234715 A1 | 9/2008 | Pesce et al. | |
| 2008/0264423 A1 * | 10/2008 | Duchon et al. | 128/830 |
| 2008/0311219 A1 | 12/2008 | Gosiewska et al. | |
| 2009/0112238 A1 | 4/2009 | Pitts et al. | |
| 2009/0187144 A1 * | 7/2009 | Jayaraman | 604/103.02 |
| 2010/0082056 A1 | 4/2010 | Mavani et al. | |
| 2010/0160819 A1 | 6/2010 | Parihar et al. | |

OTHER PUBLICATIONS

U.S. Appl. No. 12/483,305, filed Jun. 12, 2009, Hibner et al.

* cited by examiner

US 9,138,210 B2

FISTULA CLEANING AND REPAIR DEVICE AND METHOD

BACKGROUND

Fistulae can occur for a variety of reasons, such as, from a congenital defect, as a result of inflammatory bowel disease such as Crohn's disease, some sort of trauma, or as a side effect from a surgical procedure. Additionally, several different types of fistulae can occur in humans, for example, urethro-vaginal fistulae, vesico-vaginal fistulae, tracheo-esophageal fistulae, gastrointestinal fistulae, for example gastrocutaneous, enterocutaneous and colocutaneous fistulae, and any number of anorectal fistulae such as recto-vaginal fistula, recto-vesical fistulae, recto-urethral fistulae, and recto-prostatic fistulae. When fistulas form, they can track between intestinal segments or between an intestinal segment and other organs (e.g., bladder, vagina, etc.), adjacent tissue, or the skin. Fistulas are classified as internal when they communicate with adjacent organs (e.g., entero-enteric and rectovaginal fistulas, etc.) and external when they communicate with the dermal surface (e.g., enterocutaneous, peristomal and perianal fistulas, etc.).

Promoting and improving tissue healing around the fistula opening and in the fistula tract may be an important aspect of fistulae medical treatments. For instance, promoting and improving tissue healing may lead to quicker recovery times and lessen the opportunity for infection, particularly in a post-surgical context. Some advancements in the medical arts pertaining to systems, methods, and devices to promote and improve tissue healing in patients aim to add active biological components (e.g., tissue particles, stem cells, other types of cells, etc.) to a wound site (e.g., surgical site, accidental trauma site, etc.) or other defect site (e.g., caused by disease or other condition, etc.) to promote tissue regeneration or accelerate tissue healing. When adding biological components to a site, such components may be added independently or as part of a specifically designed matrix or other mixture depending on the condition being treated and goals of the treatment. Some examples of cell-based therapy technology are disclosed in U.S. Pub. No. 2008/0311219, entitled "Tissue Fragment Compositions for the Treatment of Incontinence," published Dec. 18, 2008, the disclosure of which is incorporated by reference herein. Additional examples of cell-based therapy technology are disclosed in U.S. Pub. No. 2004/0078090, entitled "Biocompatible Scaffolds with Tissue Fragments," published Apr. 22, 2004, the disclosure of which is incorporated by reference herein. Additional examples of cell-based therapy technology are disclosed in U.S. Pub. No. 2008/0071385, entitled "Conformable Tissue Repair Implant Capable of Injection Delivery," published Mar. 20, 2008, issued as U.S. Pat. No. 7,825,296 on Jan. 25, 2011, the disclosure of which is incorporated by reference herein.

Regardless of how the active biological components are delivered or applied to a site, the biological components must first be obtained and prepared. One approach for obtaining such biological components is to harvest the desired components from a healthy tissue specimen (e.g., in an adult human). Examples of devices and associated methods for collecting and processing harvested tissue are disclosed in U.S. Pub. No. 2004/0193071, entitled "Tissue Collection Device and Methods," published Sep. 30, 2004, issued as U.S. Pat. No. 7,794,408 on Sep. 14, 2010, the disclosure of which is incorporated by reference herein. Additional examples of devices and associated methods for collecting and processing harvested tissue are disclosed in U.S. Pub. No. 2005/0038520, entitled "Method and Apparatus for Resurfacing an Articular Surface," published Feb. 17, 2005, the disclosure of which is incorporated by reference herein. Additional examples of devices and associated methods for collecting and processing harvested tissue are disclosed in U.S. Pat. No. 7,611,473, entitled "Tissue Extraction and Maceration Device," issued Nov. 3, 2009, the disclosure of which is incorporated by reference herein. Additional examples of devices and associated methods for collecting and processing harvested tissue are disclosed in U.S. Pub. No. 2008/0234715, entitled "Tissue Extraction and Collection Device," published Sep. 25, 2008, issued as U.S. Pat. No. 8,034,003 on Oct. 11, 2011, the disclosure of which is incorporated by reference herein. Additional examples of devices and associated methods for processing harvested tissue are disclosed in U.S. Pub. No. 2005/0125077, entitled "Viable Tissue Repair Implants and Methods of Use," published Jun. 9, 2005, issued as U.S. Pat. No. 7,901,461 on Mar. 8, 2011, the disclosure of which is incorporated by reference herein. Additional examples of devices and associated methods for collecting and processing harvested tissue are disclosed in U.S. Pat. No. 5,694,951, entitled "Method for Tissue Removal and Transplantation," issued Dec. 9, 1997, the disclosure of which is incorporated by reference herein. Additional examples of devices and associated methods for collecting and processing harvested tissue are disclosed in U.S. Pat. No. 6,990,982, entitled "Method for Harvesting and Processing Cells from Tissue Fragments," issued Jan. 31, 2006, the disclosure of which is incorporated by reference herein. Additional examples of devices and associated methods for collecting and processing harvested tissue are disclosed in U.S. Pat. No. 7,115,100, entitled "Tissue Biopsy and Processing Device," issued Oct. 3, 2006, the disclosure of which is incorporated by reference herein.

Once harvested and suitably processed (e.g., incorporated with a scaffold, etc.), biological material such as tissue fragments may be applied to a wound site or other type of site within the human body in a variety of ways. Various methods and devices for applying such biological material are disclosed in one or more of the U.S. patent references cited above. Additional methods and devices for applying such biological material are disclosed in U.S. Pub. No. 2005/0113736, entitled "Arthroscopic Tissue Scaffold Delivery Device," published May 26, 2005, issued as U.S. Pat. No. 8,673,021 on Mar. 18, 2014, the disclosure of which is incorporated by reference herein.

While a variety of devices and techniques may exist for harvesting, processing, and applying biological components from a tissue specimen, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings. In the drawings, like numerals represent like elements throughout the several views.

Figure 1:
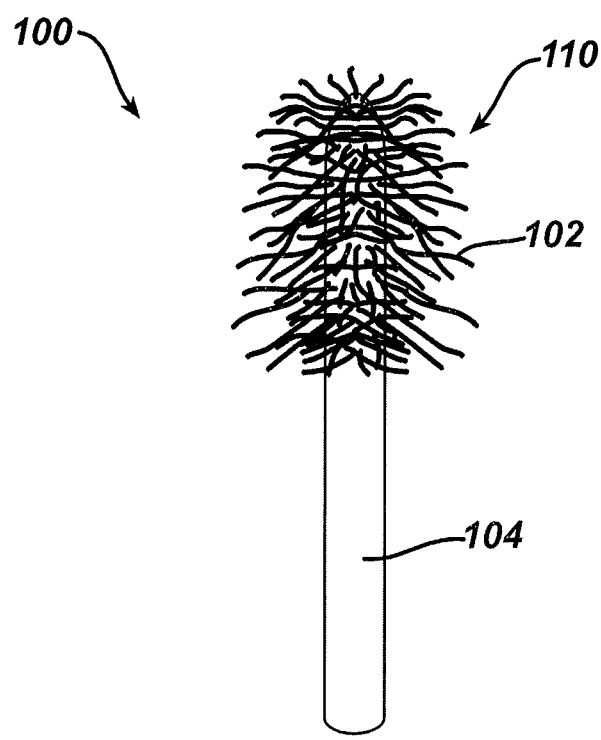
FIG. 1 depicts a side view of an exemplary fistula cleaning device end effector.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples should not be used to limit the scope of the present invention. Other features, aspects, and advantages of the versions disclosed herein will become apparent to those skilled in the art from the following description, which is by way of illustration, one of the best modes contemplated for carrying out the invention. As will be realized, the versions described herein are capable of other different and obvious aspects, all without departing from the invention. Accordingly, the drawings and descriptions should be regarded as illustrative in nature and not restrictive.

I. Overview of Exemplary Treatment Compositions, Devices, and Methods

Examples described herein include devices that are operable to clean a target site in a patient, dispense a medical fluid at a target site in a patient, and/or otherwise treat a target site in a patient. As described in greater detail below, the medical fluid may include any of a variety of biocompatible materials that accelerate tissue healing, promote tissue regeneration, and/or provide other results. As used herein, the terms "tissue treatment composition," "tissue repair composition," and "medical fluid" should be read interchangeably. It should also be understood that a tissue treatment composition or medical fluid as referred to herein may have any suitable consistency, including but not limited to the consistency of a slurry.

A medical fluid as referred to herein may be derived from any biocompatible material, including but not limited to synthetic or natural polymers. The consistency of the medical fluid may be viscous, or gel-like, that of a slurry composed of microparticles, or any other suitable consistency. By way of example only, any fluid consistency that may permit injection through a catheter may be used. The medical fluid may also provide adhesive characteristics, such that once it is injected at a target site (e.g., into a fistula), the fluid coagulates or gels (e.g., allowing for a plug to be retained within a fistula). The medical fluid of the present example is also able to support cell migration and proliferation such that healing at a target site in a patient can occur. The fluid is suitable to be mixed with biological materials. Examples of medical fluid components include but are not limited to thrombin, platelet poor plasma (PPP) platelet rich plasma (PRP), starch, chitosan, alginate, fibrin, polysaccharide, cellulose, collagen, gelatin-resorcin-formalin adhesive, oxidized cellulose, mussel-based adhesive, poly (amino acid), agarose, amylose, hyaluronan, polyhydroxybutyrate (PHB), hyaluronic acid, poly(vinyl pyrrolidone) (PVP), poly(vinyl alcohol) (PVA), polylactide (PLA), polyglycolide (PGA), polycaprolactone (PCL), and their copolymers, VICRYL® (Ethicon, Inc., Somerville, N.J.), MONOCRYL material, PANACRYL (Ethicon, Inc., Somerville, N.J.), and/or any other material suitable to be mixed with biological material and introduced to a wound or defect site, including combinations of materials. Other suitable compounds, materials, substances, etc., that may be used in a medical fluid will be apparent to those of ordinary skill in the art in view of the teachings herein.

By way of example only, one or more components in a medical fluid or tissue treatment composition may comprise at least one viable tissue fragment having one or more viable cells that, once applied, can proliferate and integrate with tissue at a target site in a patient. For instance, viable cells may migrate out of a tissue particle and populate a scaffold material, which may be positioned at a target site in a patient. Such tissue fragments may have been harvested from the same patient in whom they are reapplied; or may have been harvested from another person or source. The tissue fragments may comprise autogenic tissue, allogenic tissue, xenogenic tissue, mixtures of any of the foregoing, and/or any other type(s) of tissue. The tissue fragments may include, for example, one or more of the following tissues or tissue components: stem cells, cartilage tissue, meniscal tissue, ligament tissue, tendon tissue, skin tissue, muscle tissue (e.g., from the patient's thigh, etc.), periosteal tissue, pericardial tissue, synovial tissue, fat tissue, bone marrow, bladder tissue, umbilical tissue, embryonic tissue, vascular tissue, blood and combinations thereof. Of course, any other suitable type of tissue may be used, including any suitable combination of tissue types. In some versions, the type of tissue used is selected from a tissue type most resembling the tissue at, near, or surrounding the target site (e.g., fistula, etc.).

Tissue for providing at least one viable tissue fragment may be obtained using any of a variety of tissue biopsy devices or using other types of tissue harvesting devices or techniques. Exemplary biopsy devices include those taught in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2007/0118048, entitled "Remote Thumbwheel for a Surgical Biopsy Device," published May 24, 2007, issued as U.S. Pat. No. 7,442,171 on Oct. 28, 2008; U.S. Pub. No. 2008/0214955, entitled "Presentation of Biopsy Sample by Biopsy Device," published Sep. 4, 2008; U.S. Non-Provisional patent application Ser. No. 12/337,942, entitled "Biopsy Device with Central Thumbwheel," filed Dec. 18, 2008, published as U.S. Pub. No. 2010/0160819 on Jun. 24, 2010, now abandoned; and U.S. Non-Provisional patent application Ser. No. 12/483,305, entitled "Tetherless Biopsy Device with Reusable Portion," filed Jun. 12, 2009, issued as U.S. Pat. No. 8,206,316 on Jun. 26, 2012. The disclosure of each of the above-cited U.S. patents, U.S. patent application Publications, and U.S. Non-Provisional patent applications is incorporated by reference herein. Such biopsy devices may be used to extract a plurality of tissue specimens from one or more sites in a single patient. It should also be understood that any suitable device described in any other reference that is cited herein may be used to harvest tissue. Other examples will be apparent to those of ordinary skill in the art in view of the teachings herein. Tissue harvesting sites may include the same sites in which tissue is reapplied as part of a treatment. In addition or in the alternative, tissue may be harvested from one site and then reapplied at some other site as part of a treatment. In some versions, the tissue is reapplied in the same patient from whom the tissue was originally harvested. In some other versions, the tissue is applied in a patient who is different from the patient from whom the tissue was originally harvested.

A tissue specimen may be obtained under aseptic conditions, and then processed under sterile conditions to create a suspension having at least one minced, or finely divided, tissue fragment. In other words, harvested tissue may be diced, minced or morcellated, and/or otherwise processed. Harvested tissue specimens may be minced and otherwise processed in any of a variety of ways. For instance, examples of tissue mincing and processing are described in U.S. Pub. No. 2004/0078090, the disclosure of which is incorporated by reference herein. In order to ensure viability of the tissue, agitators or other features of a mincing and/or mixing device may be designed to sever and mix (rather than crush or compress) the tissue. In some settings, tissue specimens may be minced and/or mixed in a standard cell culture medium, either in the presence or absence of serum. Tissue fragments may also be contacted with a matrix-digesting enzyme to facilitate cell migration out of an extracellular matrix surrounding the cells. Suitable matrix-digesting enzymes that may be used in some settings include, but are not limited to, collagenase, chondroitinase, trypsin, elastase, hyaluronidase, peptidase, thermolysin, and protease. The size of each tissue fragment may vary depending on the target location, method for delivering the treatment composition to the target site, and/or based on various other considerations. For example, the tissue fragment size may be chosen to enhance the ability of regenerative cells (e.g., fibroblasts) in the tissue fragments to migrate out of the tissue fragments, and/or to limit or prevent the destruction of cell integrity. In some settings, ideal tissue fragments are between approximately 200 microns and approximately 500 microns in size. As another merely illustrative example, ideal tissue fragments may be sized within the range of approximately 0.05 mm$^3$ and approximately 2 mm$^3$; or more particularly between approximately 0.05 mm$^3$ and approximately 1 mm$^3$. Of course, various other tissue fragment sizes may be ideal in various different settings.

In some versions, a medical fluid may comprise minced tissue fragments suspended in a biocompatible carrier. Suitable carriers may include, for example, a physiological buffer solution, a flowable gel solution, saline, and water. In the case of gel solutions, the tissue repair composition may be in a flowable gel form prior to delivery at the target site, or may form a gel and remain in place after delivery at the target site. Flowable gel solutions may comprise one or more gelling materials with or without added water, saline, or a physiological buffer solution. Suitable gelling materials include biological and synthetic materials. Exemplary gelling materials include the following: proteins such as collagen, collagen gel, elastin, thrombin, fibronectin, gelatin, fibrin, tropoelastin, polypeptides, laminin, proteoglycans, fibrin glue, fibrin clot, platelet rich plasma (PRP) clot, platelet poor plasma (PPP) clot, self-assembling peptide hydrogels, Matrigel or atelocollagen; polysaccharides such as pectin, cellulose, oxidized regenerated cellulose, chitin, chitosan, agarose, or hyaluronic acid; polynucleotides such as ribonucleic acids or deoxyribonucleic acids; other materials such as alginate, cross-linked alginate, poly(N-isopropylacrylamide), poly(oxyalkylene), copolymers of poly(ethylene oxide)-poly(propylene oxide), poly(vinyl alcohol), polyacrylate, or monostearoyl glycerol co-Succinate/polyethylene glycol (MGSA/PEG) copolymers; and combinations of any of the foregoing. In addition to providing a flowable carrier solution for tissue fragments, a gelling agent(s) may also act as an adhesive that anchors the tissue repair composition at the target site. In some versions, an additional adhesive anchoring agent may be included in the tissue repair composition or medical fluid. Also, one or more cross-linking agents may be used in conjunction with one or more gelling agents in order to cross-link the gelling agent.

The concentration of tissue fragments in a carrier and/or one or more medical fluid components may vary depending on the target site location, method for delivering the treatment composition to the target site, and/or for various other reasons. By way of example, the ratio of tissue fragments to carrier (by volume) may be in the range of about 2:1 to about 6:1, or in the range of about 2:1 to about 3:1. The medical fluid may also include one more additional healing agents, such as biological components that accelerate healing and/or tissue regeneration. Such biological components may include, for example, growth factors, proteins, peptides, antibodies, enzymes, platelets, glycoproteins, hormones, cytokines, glycosaminoglycans, nucleic acids, analgesics, viruses, isolated cells, or combinations thereof. The medical fluid may further include one or more additional treatment components that prevent infection, reduce inflammation, prevent or minimize adhesion formation, and/or suppress the immune system. In some versions where a scaffold is used in conjunction with a tissue treatment composition, one or more of these additional biological components or additional treatment components may be provided on and/or within the scaffold. Similarly, in some versions where a scaffold plug is used in conjunction with a tissue repair composition, one or more of these additional biological components or additional treatment components may be provided on and/or within the scaffold plug. Some examples described herein may also include one or more adhesive agents in conjunction with viable tissue fragments.

As noted above, the harvested tissue may be combined with a scaffold material and/or other substances as part of a medical fluid, as described herein, for administration to the patient. To the extent that tissue is incorporated with a scaffold material, it should be understood that any suitable material or combination of materials may be used to provide a scaffold. By way of example only, scaffold material may include a natural material, a synthetic material, a bioabsorbable polymer, a non-woven polymer, other types of polymers, and/or other types of materials or combinations of materials. Examples of suitable biocompatible materials include starch, chitosan, cellulose, agarose, amylose, lignin, hyaluronan, alginate, hyaluronic acid, fibrin glue, fibrin clot, collagen gel, gelatin-resorcin-formalin adhesive, platelet rich plasma (PRP) gel, platelet poor plasma (PPP) gel, Matrigel, Monostearoyl Glycerol co-Succinate (MGSA), Monostearoyl Glycerol co-Succinate/polyethylene glycol (MGSA/PEG) copolymers, laminin, elastin, proteoglycans, polyhydroxybutyrate (PHB), polyvinyl pyrrolidone) (PVP), polylactide (PLA), polyglycolide (PGA), polycaprolactone (PCL), and their copolymers, non-woven VICRYL® (Ethicon, Inc., Somerville, N.J.), MONOCRYL material, fibrin, non-woven poly-L-lactide, and non-woven PANACRYL (Ethicon, Inc., Somerville, N.J.). Polymers may include aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, polypropylene fumarate), polyurethane, poly(ester urethane), poly(ether urethane), and blends and copolymers thereof. Suitable synthetic polymers for use in examples described herein may also include biosynthetic polymers based on sequences found in collagen, laminin, glycosaminoglycans, elastin, thrombin, fibronectin, starches, poly(amino acid), gelatin, alginate, pectin, fibrin, oxidized cellulose, chitin, chitosan, tropoelastin, hyaluronic acid, silk, ribonucleic acids, deoxyribonucleic acids, polypeptides, proteins, polysaccharides, polynucleotides, and combinations thereof. Other suitable materials or combinations of materials that may be used will be apparent to those of ordinary skill in the art in view of the teachings herein. It should also be understood that tissue mixed with a scaffold material may have any suitable particle size, and that the resulting mixture may at least initially have the consistency of a slurry or have any other suitable consistency. In some versions, the tissue particles include an effective amount of viable cells that can migrate out of the tissue particle and populate the scaffold. The term "viable," as used herein, should be understood to include a tissue sample having one or more viable cells.

In some versions, one or more components in a medical fluid or tissue treatment composition comprise one or more healing agents that promote tissue regeneration at a target site (e.g., within a fistula) and/or accelerate tissue healing at the target site. Healing agents may include any of a variety of biocompatible materials that accelerate tissue healing and/or promote tissue regeneration. Such biological components may include, for example, growth factors, proteins, peptides, antibodies, enzymes, platelets, glycoproteins, hormones, cytokines, glycosaminoglycans, nucleic acids, analgesics, viruses, isolated cells, or combinations thereof. The medical fluid may further include one or more additional treatment components that prevent infection, reduce inflammation, prevent or minimize adhesion formation, and/or suppress the immune system. In some versions where a scaffold is used in conjunction with a tissue treatment composition, one or more of these additional biological components or additional treatment components may be provided on and/or within the scaffold. Some examples described herein may also include one or more adhesive agents in conjunction with viable tissue fragments.

Examples described herein relate to the repair (e.g., closing) of lumens in a patient, such as anal fistulas and other types of fistulas. In particular, examples described herein include devices used in at least part of a process to deliver tissue repair compositions or medical fluid into a lumen such as an anal fistula. It should be understood that anal fistulas and/or other types of fistulas may be relatively difficult to repair (e.g., close) in some settings. The goal of a surgical repair of an anal fistula may be to close the fistula with as little impact as possible on the sphincter muscles. In some settings, a tissue repair composition or medical fluid as described herein may be delivered into the fistula as a liquid composition, a flowable gel or paste, a scaffold plug, or a combination of the two or more of the foregoing (e.g., a porous scaffold plug loaded with a medical fluid composition, etc). Anal fistulas may also be repaired by injecting bioresorbable fibrin glue into the fistula that seals the fistula and promotes tissue growth across the fistula in order to provide permanent closure. Various bioresorbable plugs may also be used to repair anal fistulas. The plug may comprise, for example, collagen protein, tissue, stem cells, and/or other medical fluid components referred to herein; and the plug may be inserted into the fistula where it promotes tissue growth across the fistula as the plug dissolves. If desired, the plug may be secured in place using one or more fasteners and/or one or more adhesive agents. As another merely illustrative example, a medical fluid may be introduced within the fistula, and the medical fluid may eventually harden and then dissolve and/or be absorbed.

Prior to applying a medical fluid to a fistula, it may be desirable in some settings to clean the wall of a fistula, otherwise agitate the wall of the fistula, and/or otherwise treat the walls of the fistula. This cleaning process may include debriding the fistula (e.g., removing epithelial cells from the wall of the fistula, etc.) and/or otherwise agitating the tissue forming the wall of the fistula. Tissue loosened as part of the debriding process may be removed from the fistula using a vacuum, by flushing with a liquid (e.g., saline), and/or in other ways. Merely illustrative examples of how the walls of a fistula may be treated and how a medical fluid may be applied in a fistula will be described in greater detail below. While examples herein are discussed in the context of an anorectal fistula, it should be understood that the following exemplary devices and techniques may be readily applied to various other types of fistulae. Similarly, while the present example relates to treatment of a fistula in a patient, it should also be understood that the following exemplary devices and techniques may be readily applied with respect to various other types of conditions in a patient. Other suitable ways in which the devices and techniques described herein may be used will be apparent to those of ordinary skill in the art in view of the teachings herein.

As used herein, the term "fluid communication" (or in some contexts "communication") means that there is a path or route through which fluid (gas, liquid or other flowable material) may flow between two components, either directly or through one or more intermediate components. Similarly, the term "conduit" encompasses a conduit within or integrated with a valve. In other words, fluid communication between two components means that fluid can flow from one component to another but does not exclude an intermediate component (e.g., a valve, etc.) between the two recited components that are in fluid communication. Similarly, two or more components may be in mechanical "communication" with each other even if intermediate components are interposed between those two or more components.

II. Exemplary Fistula Cleaning Device with Debriding Head

FIG. 1 depicts an exemplary version of a fistula cleaning device (100). Fistula cleaning device (100) comprises a head (110) and a shaft (104) connected to head (110). Head (110) has a generally cylindrical shape and also has a diameter small enough such that head (110) may be inserted into a fistula. However, head (110) may be any dimension and/or shape (e.g., spherical, etc.). Head (110) comprises a plurality of bristles (102) extending outward from the center of head (110). Bristles (102) are flexible enough to allow head (110) to be inserted in a fistula without causing undesirable trauma; yet are rigid enough to debride the wall of the fistula. Bristles (102) cover at least a portion of head (110) and are spread out uniformly around the circumference of head (110). Alternatively, bristles (102) may cover only a select portion of head (110). Bristles (102) are positioned on head (110) so as to extend outward in a generally straight path. Alternatively, bristles (102) may be configured and positioned such that bristles (102) extend outward in crossing paths or curved paths, etc. In the illustrated version, bristles (102) comprise a metal wire brush material. By way of example only, bristles (102) may be formed of 300 series stainless steel, titanium, nylon high density polyethylene, or combinations thereof. Various other types of materials that may be used to form bristles (102) will be apparent to one of ordinary skill in the art in view of the teachings herein.

Head (110) is rigidly secured to shaft (104), which also has a generally cylindrical shape. Shaft (104) is constructed of a flexible material such that shaft (104) may be guided through a fistula. Shaft (104) may also have a porous and/or abrasive outer surface so as to provide an abrasive contact with the wall of a fistula. The outer surface of shaft (104) may thus be used to rub against the fistula walls and loosen tissue that bulges through the porous outer surface or otherwise engages the outer surface when shaft (104) is inserted into the fistula. In versions where shaft (104) has pores or other openings formed through its outer surface, loosened tissue may enter an interior portion of shaft (104) for removal. In addition, loosened tissue may be removed using a vacuum, using a liquid (e.g., saline) to flush the fistula, and/or using any other suitable techniques. To the extent that shaft (104) has pores or other openings, shaft (104) may be further configured to deliver a medical fluid to the fistula. Such a medical fluid may have a composition as described herein or any other suitable composition.

Figure 2:
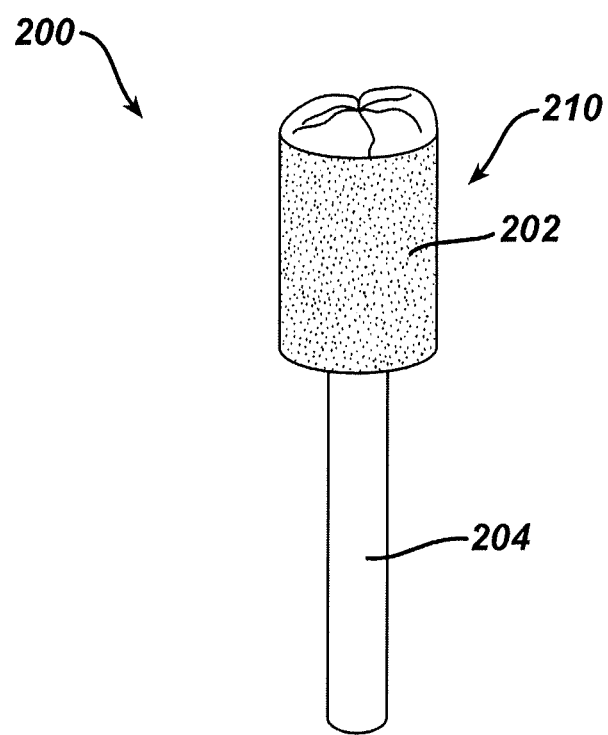
FIG. 2 depicts a side view of an exemplary alternative fistula cleaning device end effector.

FIG. 2 depicts another exemplary fistula cleaning device (200). Fistula cleaning device (200) of this example comprises a head (110) and a shaft (204) connected to head (210). Head (210) has a generally solid cylindrical shape and also has a diameter small enough such that head (210) may be inserted into a fistula. However, head (210) may be any dimension and/or shape (e.g., spherical, cylindraceous with rounded distal end like a bullet, etc.). The outer surface of head (210) is constructed of a rough material having a high coefficient of friction such that the outer surface debrides tissue when it moves against tissue in a fistula. For instance, head (210) may include a fine grit, a coarse grit, or combinations thereof. Head (210) may comprise various materials, including but not limited to plastics (e.g., nylon, liquid crystal polymer such as Vectra, polyethylene, Ultem, polycarbonate, etc.) and/or powder metal (e.g., titanium, 400 series stainless steel, etc.). Various other types of materials that may be used to form head (210) will be apparent to one of ordinary skill in the art in view of the teachings herein. It should also be understood that head (210) may be formed with grit-like features in addition to or in lieu of having a separate grit material secured to head (210). Shaft (204) may be configured and operable in accordance with the configuration and operability described above with respect to shaft (104). Alternatively, shaft (204) may have any other suitable configuration and/or operability.

Figure 3:
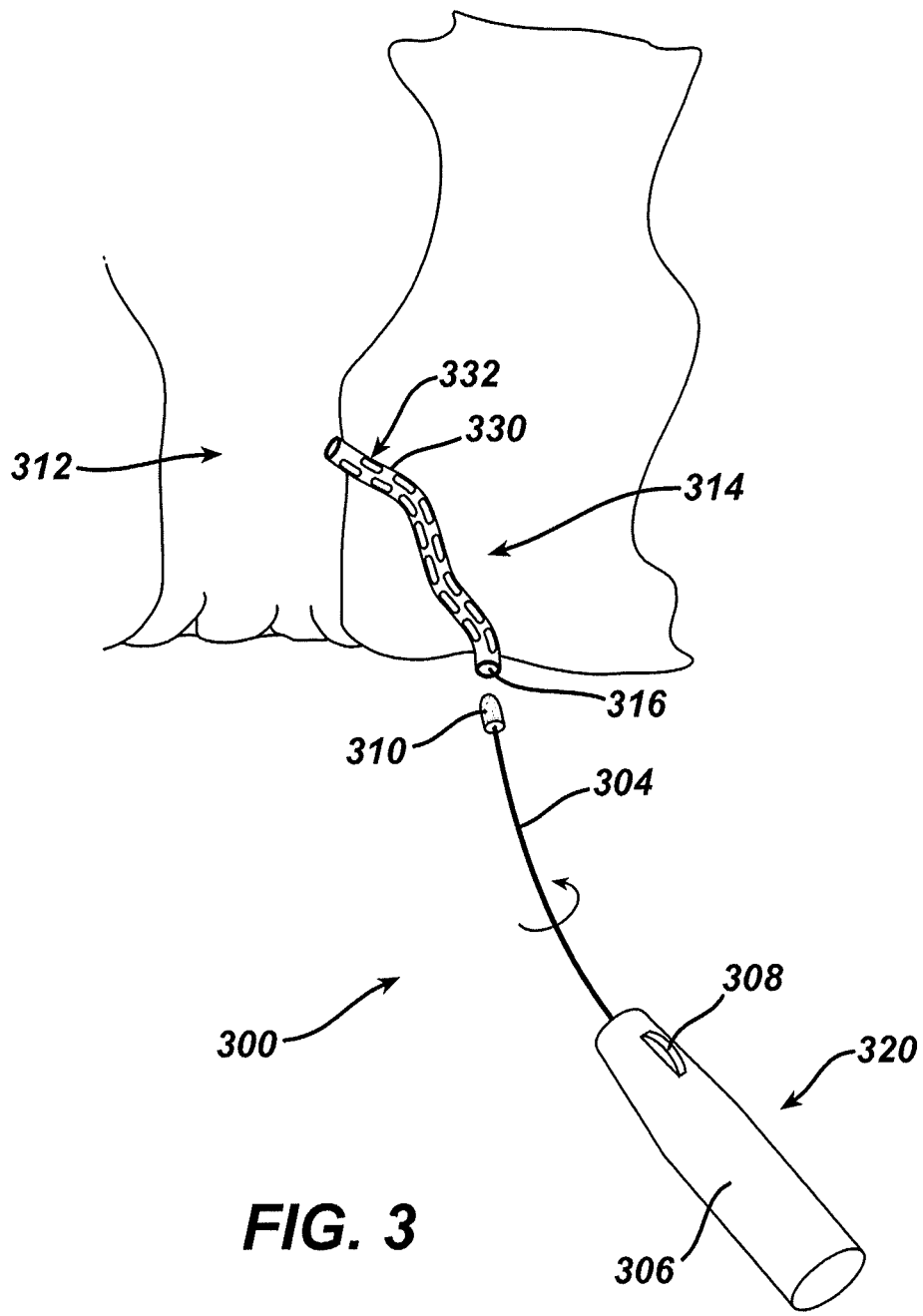
FIG. 3 depicts a perspective view of yet another exemplary alternative fistula cleaning device being used to clean a fistula.

FIG. 3 shows one exemplary method of using a fistula cleaning device (300) to clean a fistula (314). Fistula cleaning device (300) comprises a handpiece (320), a shaft (304) extending from handpiece (320), and a head (310) coupled with shaft (304). Head (310) may be configured and operable similar to head (110) or head (210) as described above; or may have any other suitable configuration. In some versions, shaft (304) is configured to interchangeably receive heads (110, 210). Shaft (304) may also be configured and operable similar to shaft (104) described above. Handpiece (320) of the present example has a gripping portion (306) and an actuation member (308). Handpiece (320) also houses a power source (not shown) and a motor (not shown) that is powered by the power source. The motor is selectively activated by actuation member (308), and is in communication with head (310). In particular, the motor is operable to rotate head (310) via shaft (304). Shaft (304) may include a rotating member (not shown) coaxially disposed in an outer sheath, with the rotating member transmitting rotary motion from the motor to head (310). Of course, a variety of other components and configurations may be used. For instance, handpiece (320) may include a crank, dial, ring, and/or other type of actuator that is operable to rotate head (310) manually. Other suitable components, configurations, and operabilities for fistula cleaning device (300) will be apparent to those of ordinary skill in the art in view of the teachings herein.

Fistula cleaning device (300) may be used to clean a fistula (314) that extends from a patient's rectum (312) to an external entrance (316) of fistula (314). Of course, fistula cleaning device (300) may instead be used to clean any type of fistula or various other anatomical features. As a merely illustrative example of this process, a flexible tube (330) may first be inserted into fistula (314). Flexible tube (330) of this example includes a plurality of transverse openings (332) formed along its length. In addition, flexible tube (330) of this example is flexible enough to pass along a tortuous or curved path of fistula (314); yet is rigid enough to resist collapsing once positioned in fistula (314). With flexible tube (330) positioned within fistula (314), the tissue lining the wall of fistula (314) prolapses and protrudes through openings (332) of flexible tube (330). Head (310) is then inserted into fistula (314) via entrance (316), and through inserted flexible tube (330). Once in fistula (314), head (310) is rotated and/or longitudinally reciprocated within fistula (314) to debride the tissue protruding through openings (332) of flexible tube (330). Rotation of head (310) may be initiated by activating actuation member (308). Shaft (304) may also debride tissue protruding through openings (332). Head (310) may be guided through the entire length of fistula (314), or head (310) may be inserted through only a portion of the entire length of fistula (314).

Once the wall of fistula (314) has been sufficiently debrided, the user may remove fistula cleaning device (300) from fistula (314) by pulling head (310) and shaft (304) out through entrance (316). Debrided tissue may also be removed, or alternatively, may remain in fistula (314). Furthermore, the user may then inject a medical fluid as described herein into fistula (314) to promote healing of fistula (314). In some versions, flexible tube (330) is removed before medical fluid is introduced into fistula (314). In some other versions, flexible tube (330) remains in fistula (314) as medical fluid is introduced into fistula (314). By way of example only, flexible tube (330) may be formed of a bioabsorbable material. Various suitable ways in which a medical fluid may be introduced into a fistula are described herein, while other suitable ways to introduce a medical fluid into a fistula will be apparent to those of ordinary skill in the art in view of the teachings herein.

III. Exemplary Fistula Cleaning and Repair Device with Expanding Retainer

Figure 4:
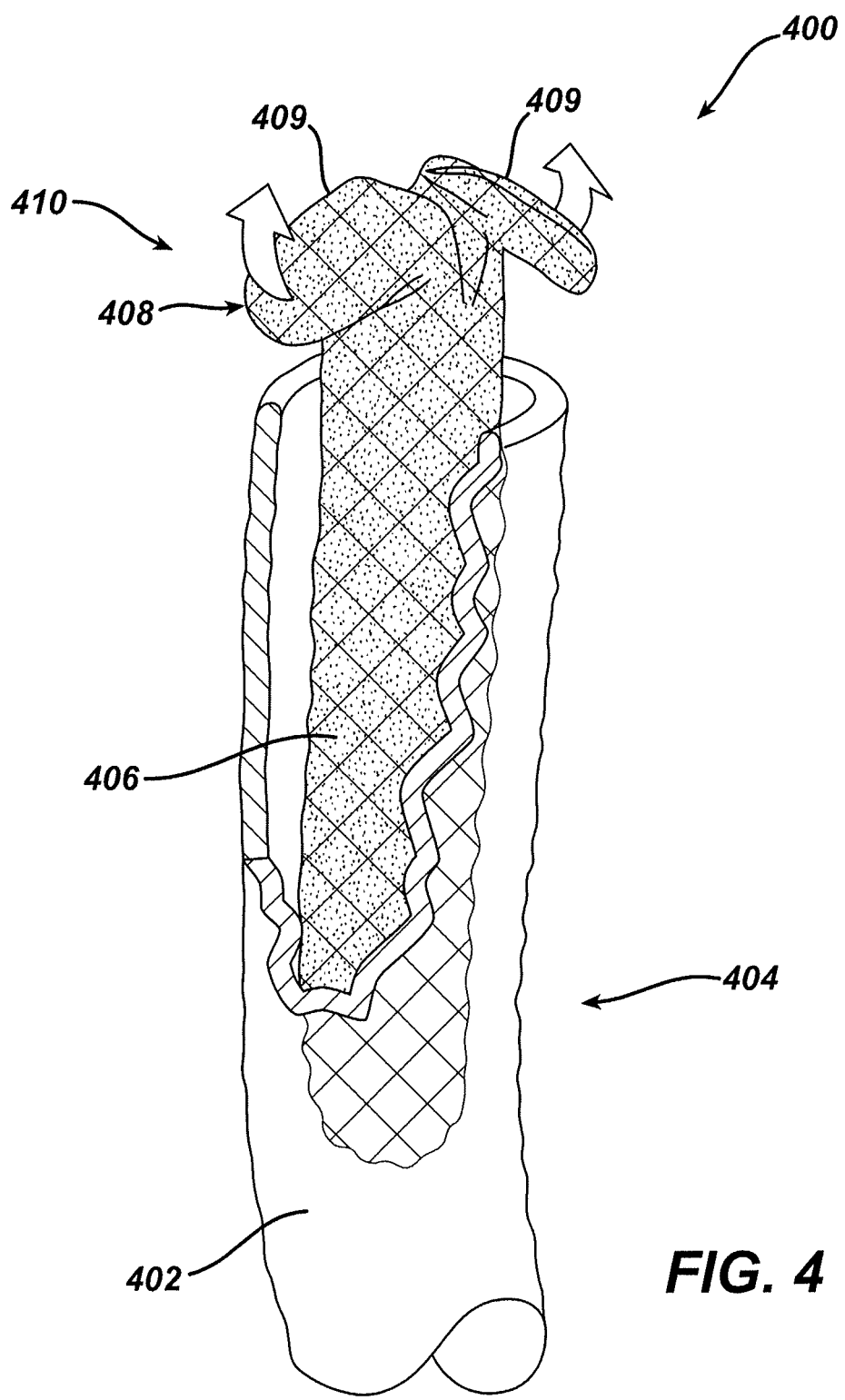
FIG. 4 depicts a side view of an exemplary fistula repair device.

FIG. 4 depicts an exemplary fistula repair device (400). Fistula repair device (400) of this example comprises a plug member (410) and a catheter (404). Plug member (410) is coaxially positioned within catheter (404). Furthermore, plug member (410) is movable within catheter (404) such that catheter (404) may maintain its position while plug member (410) is free to move through the length of catheter (404). In the present example, plug member (410) is substantially solid and comprises a lattice structure, though in some other versions plug member (410) is substantially hollow like a stent. Plug member (410) comprises a retainer portion (408) and a body portion (406). Retainer portion (408) comprises a pair of movable arms (409). In particular, movable arms (409) may be moved from a retracted position, in which they are substantially parallel to a longitudinal axis defined by plug member (410), to an outward extended position, in which they extend substantially transverse to the longitudinal axis defined by plug member (410). In the retracted position, plug member (410) may slidably move through catheter (404) and through a fistula. If the movable arms of retainer portion (408) are extended, the effective width of retainer portion (408) becomes larger such that plug member (410) may be generally unable to retract into catheter (404) once extended beyond the end of catheter (404). Furthermore, once plug member (410) is inserted into a fistula such that retainer portion (408) extends beyond an end of the fistula, extending the movable arms outward substantially prevents plug member (410) from retracting back through the fistula. Arms (409) of retainer portion (408) may be configured to remain in a retracted position when subject to compressive forces such as those applied by catheter (404) walls. However, once compressive forces have become alleviated, the arms (409) are configured to automatically expand to an outward extended position. In other words, arms (409) may be resiliently biased to assume the extended configuration, in which plug member (410) generally has a configuration similar to that of a "molly bolt." Body portion (406) of plug member (410) may comprise a flexible material and may further be cut to approximately the length of a fistula to be repaired, but any suitable length may be used. By way of example only, body portion (406) of plug member (410) may comprise a bioabsorbable polymer, a non-woven polymer, other types of polymers starch, chitosan, cellulose, agarose, amylose, lignin, hyaluronan, alginate, polyhydroxybutyrate (PHB), poly (hyaluronic acid), poly(vinyl pyrrolidone) (PVP), polylactide (PLA), polyglycolide (PGA), polycaprolactone (PCL), and their copolymers, non-woven Vicryl® (Ethicon, Inc., Somerville, N.J.), monocryl material, fibrin, non-woven poly-L-lactide, non-woven panacryl (Ethicon, Inc., Somerville, N.J.), Oxidized regenerated cellulose, collagen, cross-linked fibrous collagen hemostat, and/or various other materials, including combinations thereof.

Catheter (404) has a generally hollow cylindrical shape with an abrasive exterior surface (402). Exterior surface (402) is constructed of a rough material having a high coefficient of friction such that the outer surface debrides tissue when it moves against tissue in a fistula. For instance, exterior surface (402) may include a fine grit, a coarse grit, or combinations thereof. By way of example only, exterior surface (402) may comprise nylon, liquid crystal polymer such as Vectra, polyethylene, Ultem, Polycarbonate, etc. Various other types of materials that may be used to form exterior surface (402) will be apparent to one of ordinary skill in the art in view of the teachings herein. Catheter (404) may be constructed of a flexible material so that catheter (404) may properly flex as catheter (404) is guided through a fistula. When plug member (410) is positioned within catheter (404), plug member (410) flexes and bends with catheter (404). In addition, exterior surface (402) may be porous and/or have openings formed therethrough, such that debrided tissue may be removed through such features of exterior surface (402) and/or a medical fluid may be administered through such features of exterior surface (402) and into the fistula.

Figure 5:
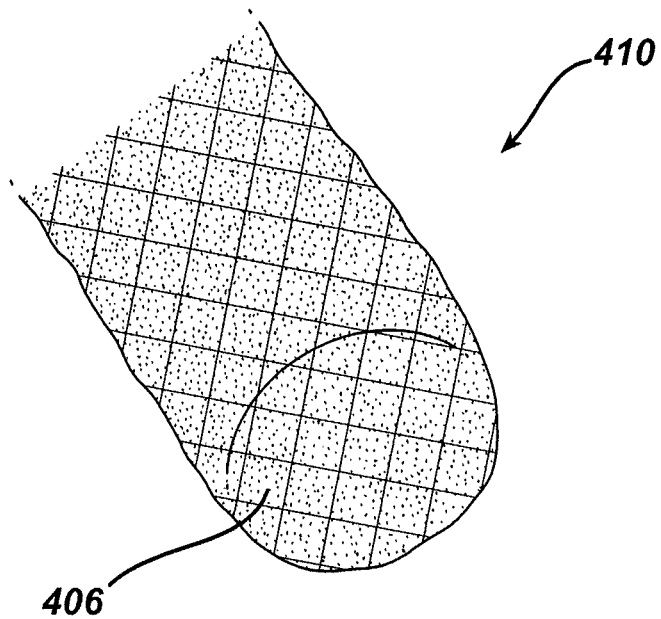
FIG. 5 depicts a perspective view of a portion of a stent of the fistula repair device of FIG. 4.
Figure 6:
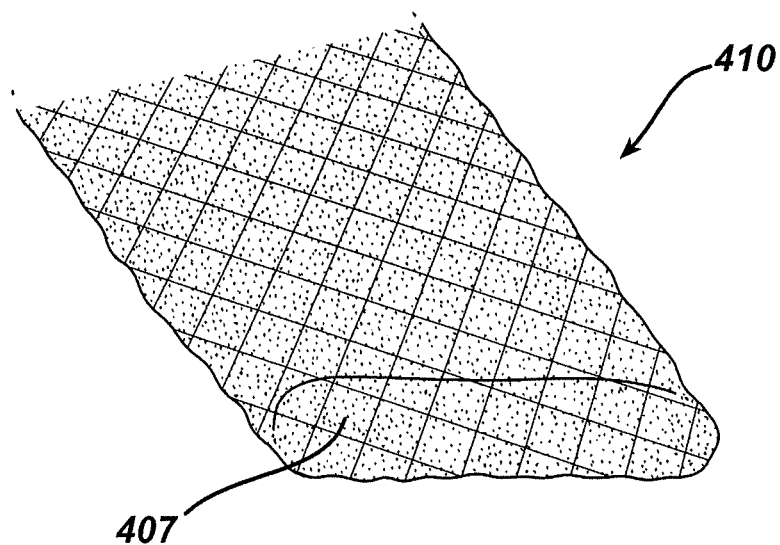
FIG. 6 depicts a perspective view of a portion of an alternative stent of the fistula repair device of FIG. 4.

As seen in FIG. 5, body portion (406) of plug member (410) may have a circular cross section. Plug member (410) may further comprise a cell matrix with a stem cell mixture such as one of the various formulations of medical fluid described herein, etc. The cell matrix may be placed in plug member (410) prior to inserting plug member (410) into a fistula. Alternatively, the cell matrix may be added after inserting plug member (410) into a fistula by injecting plug member (410) with a stem cell fluid mixture and/or other medical fluid after plug member (410) is placed within a fistula. As yet another merely illustrative variation, the material forming plug member (410) may be impregnated with or formed by medical fluid, etc. It should also be understood that the material forming plug member (410) may be bioabsorbable and/or have various other properties. In some versions, plug member (410) has a flat body portion (407) as shown in FIG. 6. However, plug member (410) may generally have any suitable shape as will be apparent to one of ordinary skill in the art in view of the teachings herein.

Figure 7:
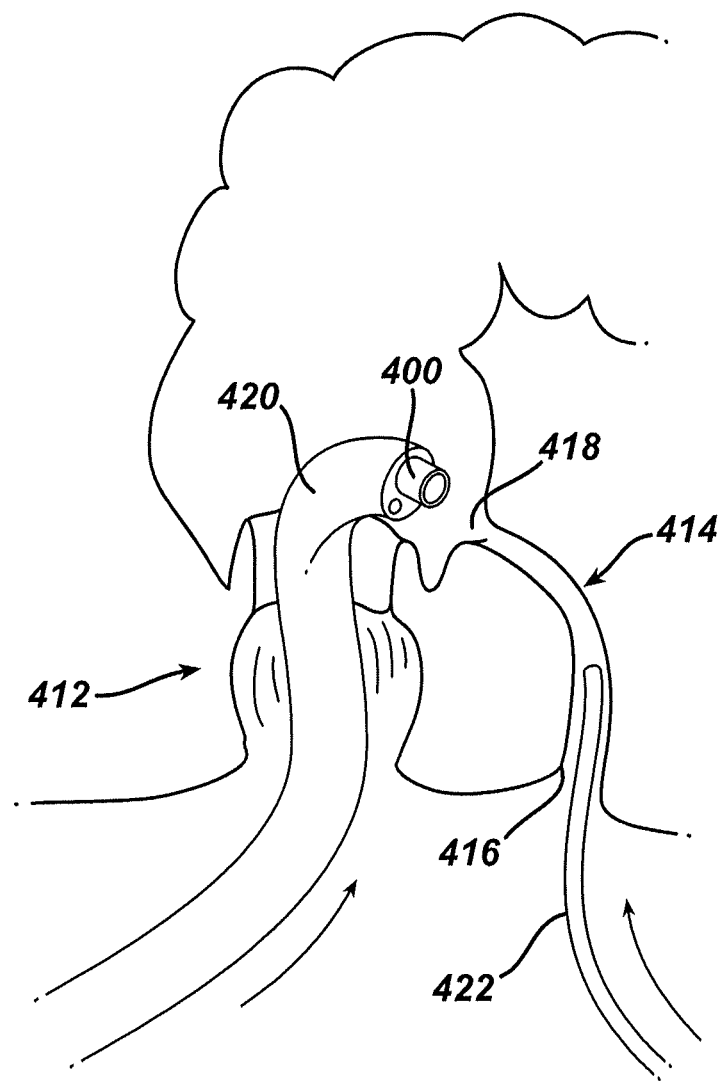
FIG. 7 depicts a perspective view of the fistula repair device of FIG. 4 inserted into a rectum to approach a fistula.
Figure 8:
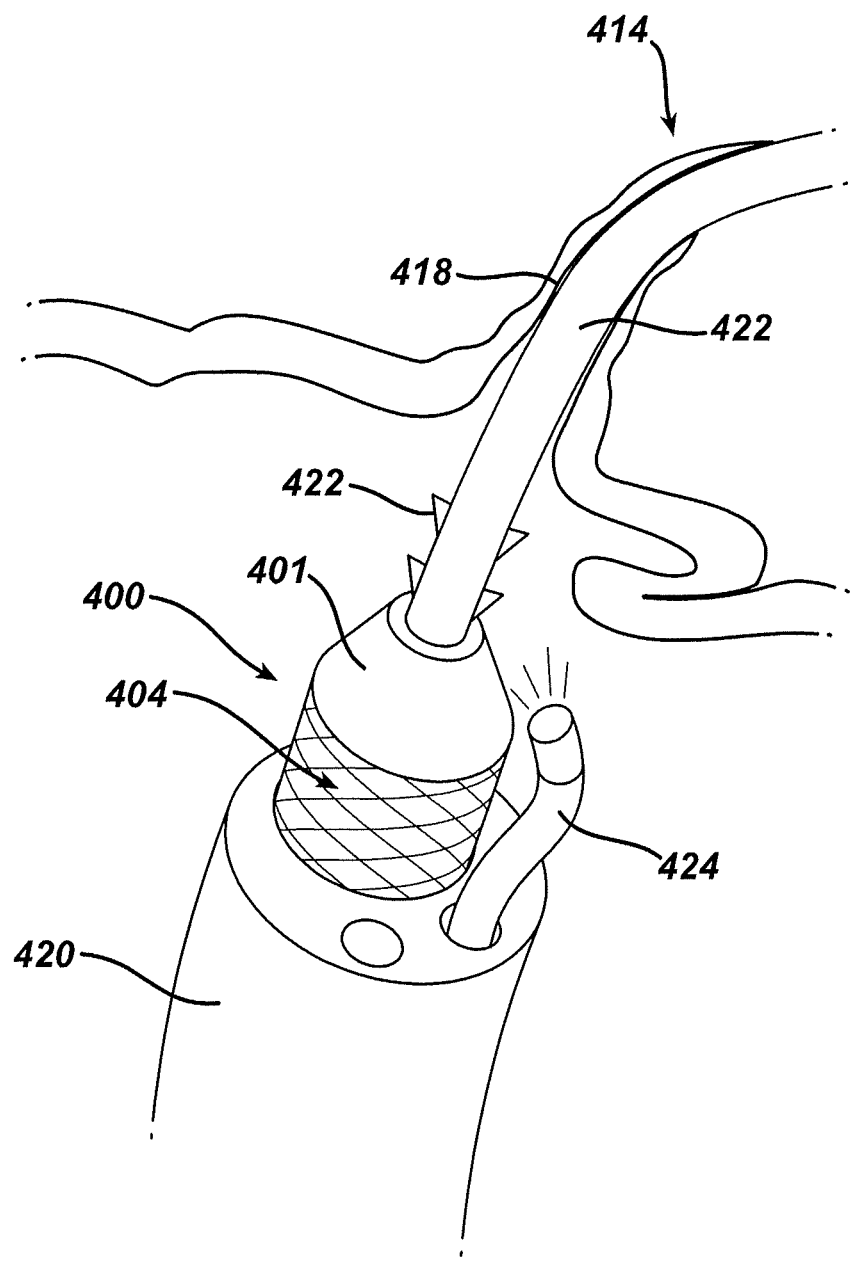
FIG. 8 depicts a partial view of the fistula repair device of FIG. 4 connecting with a guide wire inserted through the fistula.

FIGS. 7-11 depict one exemplary method of using fistula repair device (400) to repair a fistula (414). As shown in FIG. 7, fistula repair device (400) is contained inside a working channel of an endoscope (420). Endoscope (420) is inserted into the rectum (412) of a patient. Endoscope (420) is steered such that outer tube is flexed to face an inner opening (418) of fistula (414), which extends from inner opening (418) to an outer opening (416). While endoscope (420) is positioned within rectum (412), a guide wire (422) is inserted into outer opening (416) and guided through fistula (414). Guide wire (422) comprises a narrow, flexible wire capable of fitting inside of fistula (414) for coupling with fistula repair device (400) as shown in FIG. 8. In particular, guide wire (422) of the present example includes one-way barbs (422) that are configured to engage an anchor member (401) of fistula repair device (400). Anchor member (401) is fixedly secured to the distal end of catheter (404) and is positioned distal to plug member (410). Anchor member (401) includes a passageway (not shown) that is configured to receive guide wire (422) and that is engaged by barbs (422) of guide wire (422). In some other versions, guide wire (422) may include one or more hooks, graspers, a snap-fitting configured to engage a complementary snap-fitting of fistula repair device (400), or various other types of features to engage fistula repair device (400). Endoscope (420) further comprises visualization optics (424), which may be used to confirm sufficient coupling between anchor member (401) and guide wire (422).

Figure 9:
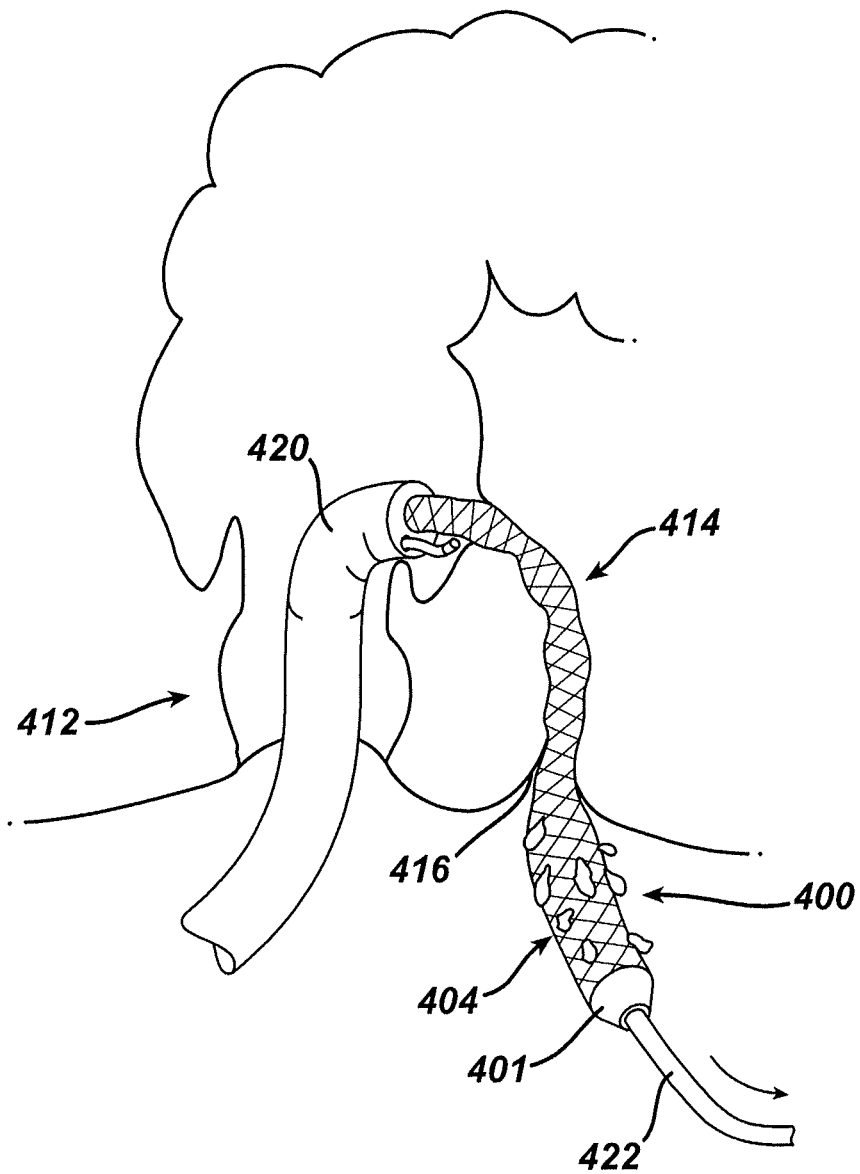
FIG. 9 depicts a perspective view of the fistula repair device of FIG. 4 being pulled through the fistula.

With guide wire (422) being sufficiently coupled with fistula repair device (400) via anchor member (401), guide wire (422) may be used to pull at least a portion of fistula repair device (400) through fistula (414) as shown in FIG. 9. As fistula repair device (400) is being pulled through fistula (414) by guide wire (422), exterior surface (402) of catheter (404) debrides the wall of fistula (414). A portion of the debrided tissue travels with catheter (404) and is eventually removed from fistula (414). It should also be understood that debrided tissue may be removed from fistula (414) using vacuum and or liquid (e.g., a saline flush, etc.). In some settings, at least some debrided tissue remains in fistula (414). With catheter (404) still being inserted through endoscope (420), a medical fluid is dispensed into plug member (410). For instance, medical fluid may be communicated distally through catheter (404) and endoscope (420) to reach plug member (410). In addition or in the alternative, anchor member (401) may contain medical fluid, and such medical fluid may be communicated proximally from anchor member (401) through catheter (404) to reach plug member (410). As yet another merely illustrative alternative, plug member (410) may already include medical fluid. Other suitable ways in which medical fluid may be provided to and/or by plug member (410) will be apparent to those of ordinary skill in the art in view of the teachings herein.

Figure 10:
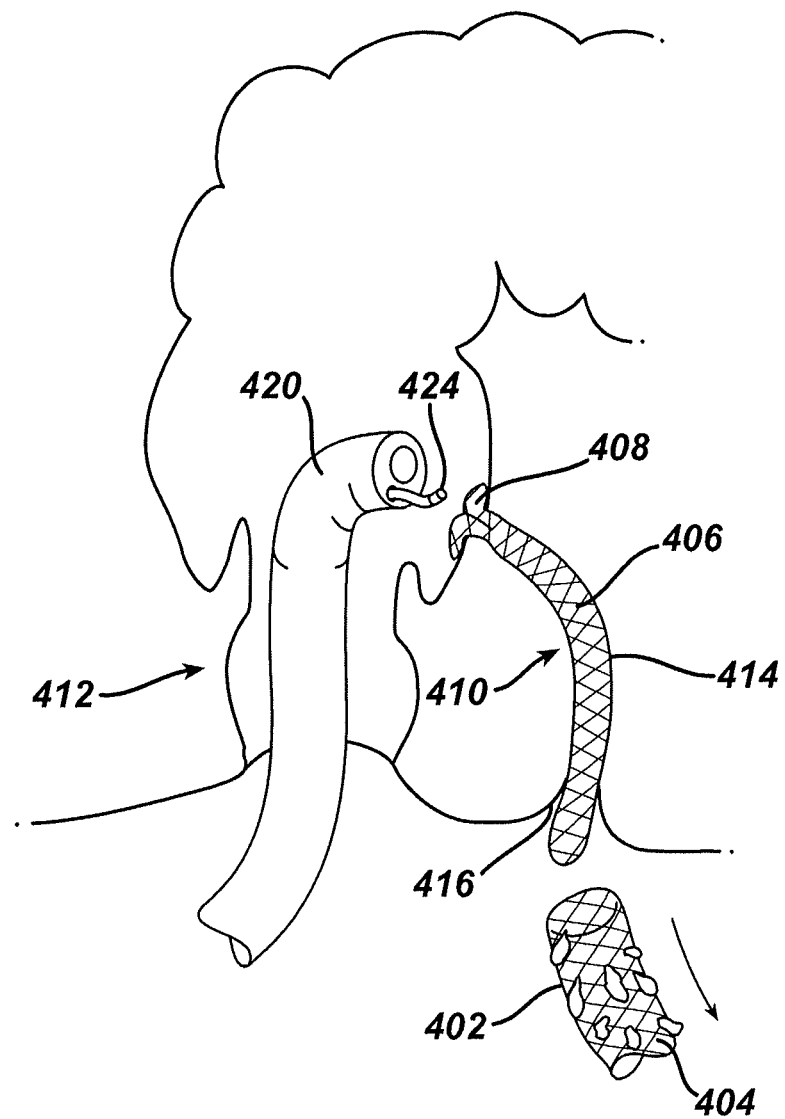
FIG. 10 depicts a perspective view of the fistula repair device of FIG. 4 with a catheter being removed.

Next, fistula repair device (400) is further removed from fistula (414) as shown in FIG. 10. In particular, catheter (404) is ultimately removed from fistula (414). As catheter (404) is pulled from fistula (414) with guide wire (422), catheter (404) also separates from plug member (410), leaving plug member (410) in fistula (414). In other words, body portion (406) and retainer portion (408) of plug member (410) become exposed to fistula (414) as catheter (404) is removed from plug member (410). In addition, plug member (410) is ultimately removed from endoscope (420).

In some versions, plug member (410) is positioned at the proximal end of catheter (404), and visualization optics (424) are used to observe when the proximal end of catheter (404) exits endoscope (420) with plug member (410). In some such versions, retainer portion (408) of plug member (410) is always exposed relative to catheter (404), such that the working channel of endoscope (420) keeps arms (409) in a retracted position until retainer portion (408) exits the working channel; and such that arms (409) resiliently extend outwardly as soon as retainer portion (408) exits the working channel of endoscope (420). After plug member (410) and catheter (404) have exited endoscope (420), plug member (410) and catheter (404) may continue to be pulled until retainer portion (408) catches on inner opening (418) of fistula (414). The resistance provided by inner opening (418) may substantially retain plug member (410) in place as catheter (404) continues to be pulled through fistula (414) until catheter (404) eventually exits outer opening (416).

In some other versions, retainer portion (408) is positioned within catheter (404) as plug member (410) and catheter (404) are pulled through the working channel of endoscope (420), such that catheter (404) keeps arms (409) in a retracted position until retainer portion (408) exits catheter (404). Visualization optics (424) are used to observe when the proximal end of catheter (404) exits endoscope (420); and when the proximal end of catheter reaches inner opening (418) of fistula (414). At this stage, plug member (410) may be pushed out of catheter (404), such that arms (409) resiliently extend outwardly as soon as retainer portion (408) exits catheter (404). For instance, once the distal end of catheter (404) has been pulled through outer opening (416) of fistula (414), catheter (404) may be grasped and held in place as guide wire (422) is pushed through catheter (404) to at least partially eject plug member (410) from catheter (404). Catheter (404) may continue to be pulled until retainer portion (408) catches on inner opening (418) of fistula (414). The resistance provided by inner opening (418) may substantially retain plug member (410) in place as catheter (404) continues to be pulled through fistula (414), until catheter (404) eventually exits outer opening (416), leaving plug member (410) disposed in fistula (414). Other suitable ways in which plug member (410) may be positioned in fistula (414) and left in fistula (414) will be apparent to those of ordinary skill in the art in view of the teachings herein.

It should be understood from the foregoing that, once retainer portion (408) is removed from endoscope (410) and catheter (404), arms (409) of retainer portion (408) resiliently deflect outwardly to prevent retainer portion (408) from passing through fistula (414). In other words, retainer portion (408) expands to present an effective width that is larger than the inner diameter of fistula (414), thereby preventing plug member (410) from traveling further through fistula (414). Visualization optics (424) may be used to determine whether plug member (410) has been properly positioned and whether retainer portion (408) has properly expanded so as to prevent further movement of plug member (410) through fistula (414). Once plug member (410) has been properly placed, endoscope (420) may be removed from rectum (412).

Figure 11:
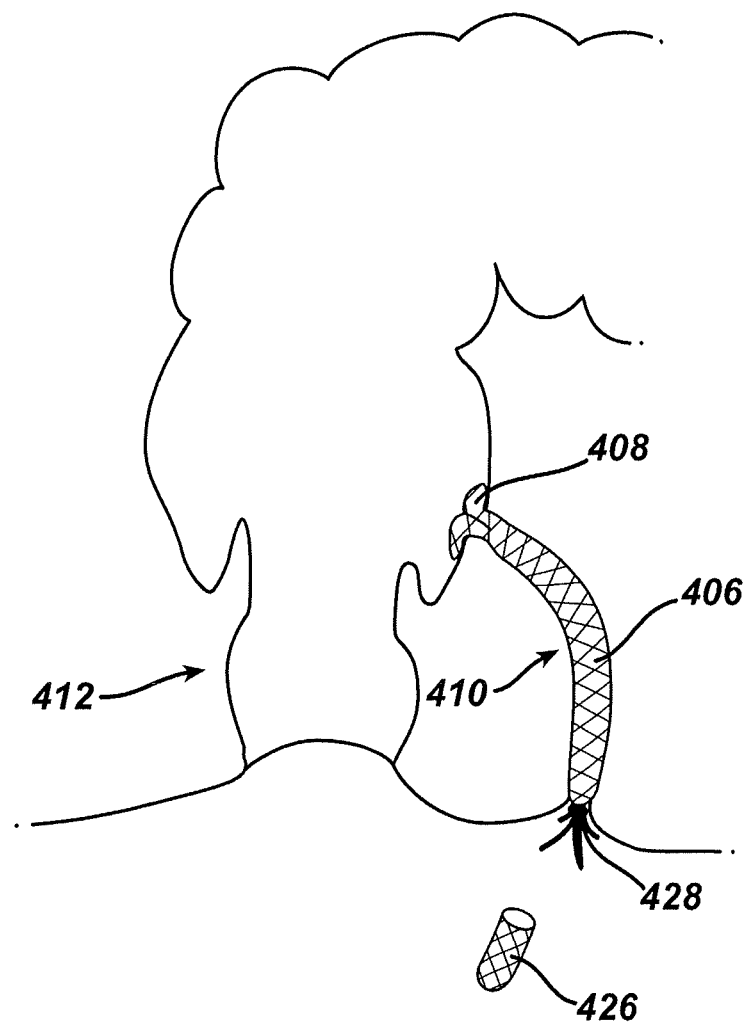
FIG. 11 depicts a perspective view of the fistula repair device of FIG. 4 with the catheter removed, with a stent positioned in the fistula, and with the fistula being sealed.
Figure 12:
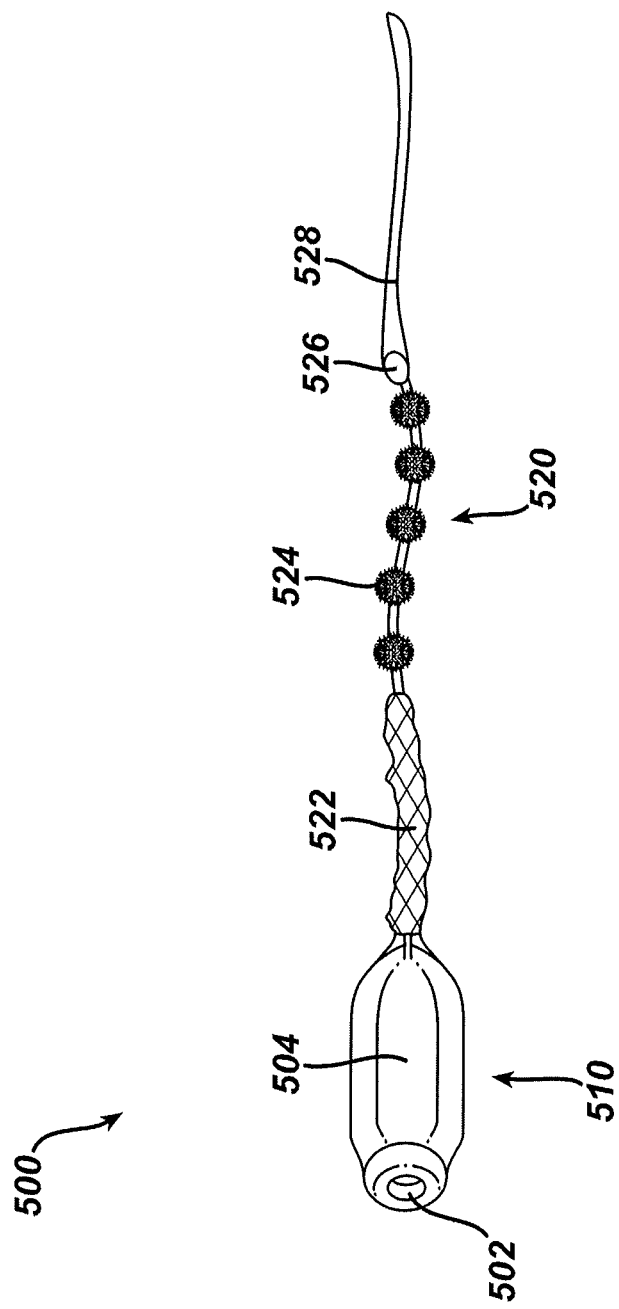
FIG. 12 depicts a side view of an exemplary alternative fistula repair device.

After endoscope (420) has been removed, retainer portion (408) continues to prevent further movement of plug member (410) through fistula (414) as shown in FIG. 11. Since plug member (410) does not have a length exactly equal to the length of fistula (414) in this example, an excess portion (426) of plug member (410) is removed by cutting. Body portion (406) of plug member (410) extends through the length of fistula (414) and is filled with a cell matrix comprising stem cells and/or some other form of medical fluid. After excess portion (426) has been removed, a sealed portion (428) is formed by, for example, suturing, RF sealing, applying bioadhesives, stapling, and/or using any other suitable devices or techniques as will be apparent to one of ordinary skill in the art in view of the teachings herein. Other suitable features, components, and configurations of fistula repair device (400) will be apparent to those of ordinary skill in the art in view of the teachings herein. Similarly, other suitable ways in which fistula repair device (400) may be used will be apparent to those of ordinary skill in the art in view of the teachings herein.

IV. Exemplary Fistula Cleaning and Repair Device with Abrasive Beads

Figure 13:
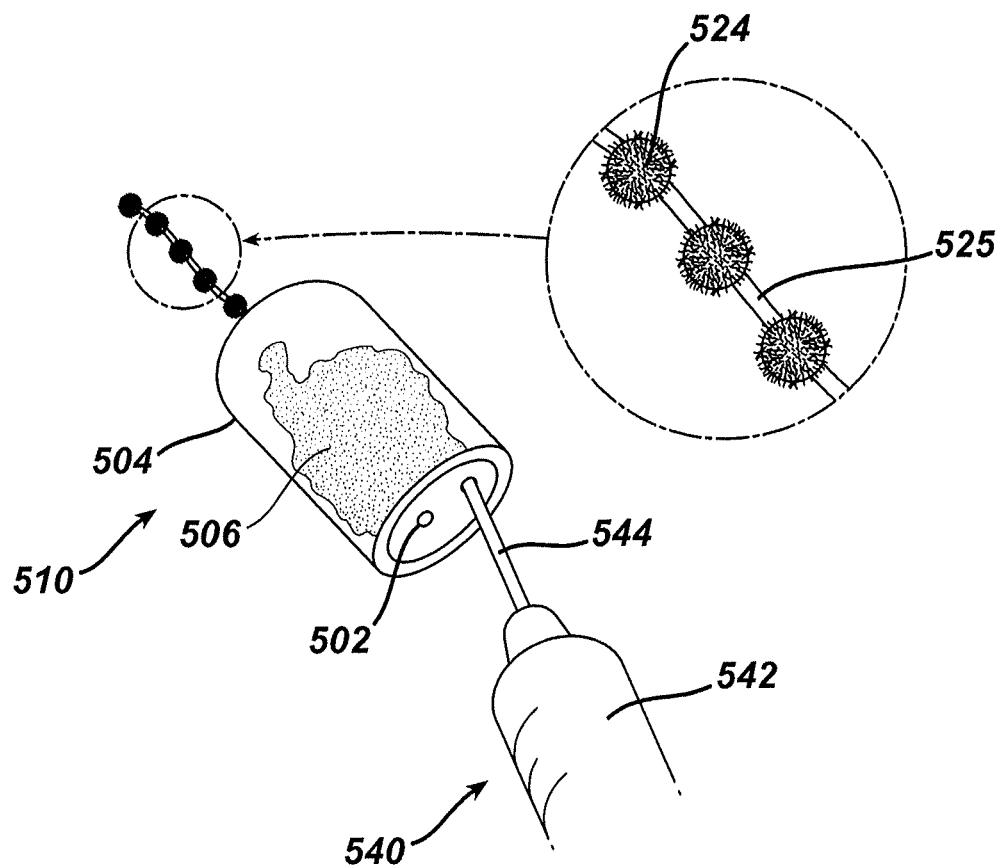
FIG. 13 depicts a partial perspective view of a proximal portion and a distal portion of the fistula repair device of FIG. 12.

FIGS. 12-16 depict another exemplary fistula repair device (500), which comprises a head portion (510), a dispensing mesh (522), a cleaning chain (520), and a threader (528). Head portion (510) comprises a material reservoir (504) configured to hold an amount of medical fluid (506). Medical fluid (506) may comprise any of the various formulations of medical fluid described herein (e.g., harvested cell tissue, a stem cell mixture, etc.). Head portion (510) also includes an injection port (502) that is in fluid communication with material reservoir (504). Injection port (502) may include a self-sealing, needle-penetrable septum and/or a variety of other types of components or features. A syringe (540) comprising a barrel (542) and a needle (544) may thus be used to add or remove medical fluid (506) to or from material reservoir (504) by inserting needle (544) into port (502) as shown in FIG. 13. While a syringe (540) is used to introduce medical fluid (506) to reservoir (504) in this example, it should be understood that medical fluid (506) may be introduced to material reservoir (504) using any other suitable devices or techniques.

Reservoir (504) of head portion (510) is in fluid communication with dispensing mesh (522), such that mesh (522) receives medical fluid (506) from head portion (510). Furthermore, mesh (522) is configured to hold medical fluid (506) within mesh (522) such that medical fluid (506) may be delivered to a fistula as described in greater detail below. In some versions, at least part of medical fluid (506) wicks through dispensing mesh (522) from reservoir (504). In addition or in the alternative, head portion (510) may comprise a piston or other feature that is operable to actively urge medical fluid (506) from reservoir (504) onto/into mesh (522). As another merely illustrative variation, a simple opening may provide substantially unobstructed communication of medical fluid (506) from reservoir (504) to mesh (522), such that any or all medical fluid (506) in reservoir (504) simply bleeds into mesh (522). As yet another merely illustrative variation, a substantial portion of mesh (522) may initially reside within reservoir (504), such that mesh (522) is saturated in medical fluid (506). Mesh (522) may then be pulled from reservoir (504) at an appropriate time, still being saturated in medical fluid (506). Other suitable ways in which mesh (522) may receive medical fluid (506) will be apparent to those of ordinary skill in the art in view of the teachings herein. Mesh (522) may comprise a woven, bioabsorbable material that may be left in the body without harming the patient. Alternatively, mesh (522) may be configured to be biologically inert so as to remain in the fistula until it is later removed.

Cleaning chain (520) is also coupled with head portion (510). Cleaning chain (520) comprises a series of abrasive beads (524). Beads (524) have an abrasive exterior surface as shown in FIG. 13. The abrasive surface of beads (524) is configured to debride the wall of a fistula such that when beads (524) are pulled through a fistula as will be described in greater detail below. While the illustrated version comprises beads (524) with an abrasive surface, it should be understood that components having various other types of features, configurations, and shapes may be used to debride a fistula. For example, beads (524) may have a rectangular shape, may comprise a series of interconnected abrasive chains, or any other suitable form as will be apparent to one of ordinary skill in the art in view of the teachings herein. Beads (524) are connected to each other by a wire (525). Alternatively, a chain or other type of structure may connect beads (524). It should also be understood that wire (525) may have a rough exterior surface to further facilitate debriding of the fistula.

Cleaning chain (520) terminates at a connecting portion (526), which couples threader (528) with cleaning chain (520). Threader (528) comprises a long and narrow member having sufficient flexibility to allow it to be fed along a tortuous or curved path of fistula; yet enough compressive strength to resist buckling as threader (528) is pushed through the fistula tract. The free end of threader (528) may be rounded to avoid causing undesirable trauma as threader (528) is pushed through the fistula tract.

Figure 14:
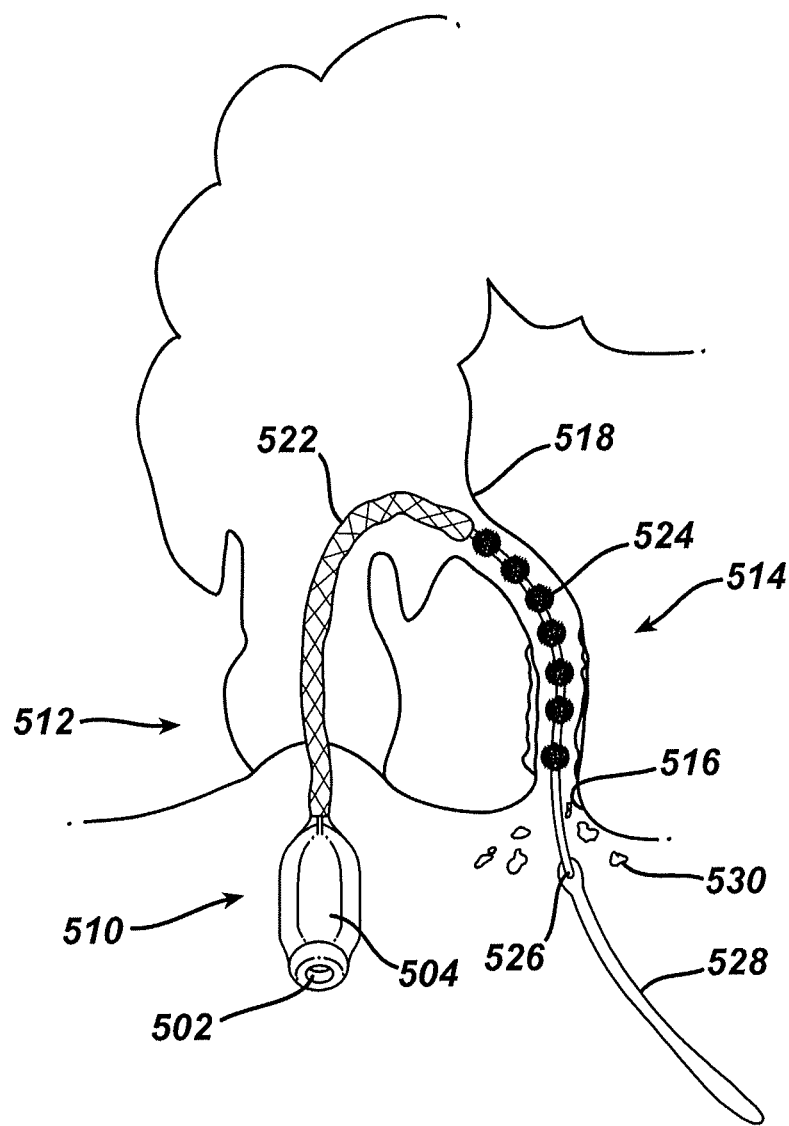
FIG. 14 depicts a perspective view of the fistula repair device of FIG. 12 inserted into a fistula.

FIGS. 14-17 depict an exemplary method of using fistula repair device (500) to repair a fistula (514), which extends from an inner opening (518) to an outer opening (516). Fistula repair device (500) may be inserted through the rectum (512) and into fistula (514) via inner opening (518), led by threader (528), as shown in FIG. 14. In particular, since threader (528) is flexible, threader (528) may be routed through rectum (512) to reach inner opening (518) of fistula (514). Once threader (528) reaches inner opening of fistula (514), head portion (510) may be pushed upward closer to rectum (512) to further urge threader (528) through fistula (514). Additionally, the user may grab or use another device to secure threader (528) to pull threader (528) through fistula (514). While threader (528) is fed through inner opening (518) toward outer opening (516) in the present example, it should be understood that threader (528) may alternatively be fed through outer opening (516) toward inner opening (518).

Figure 15:
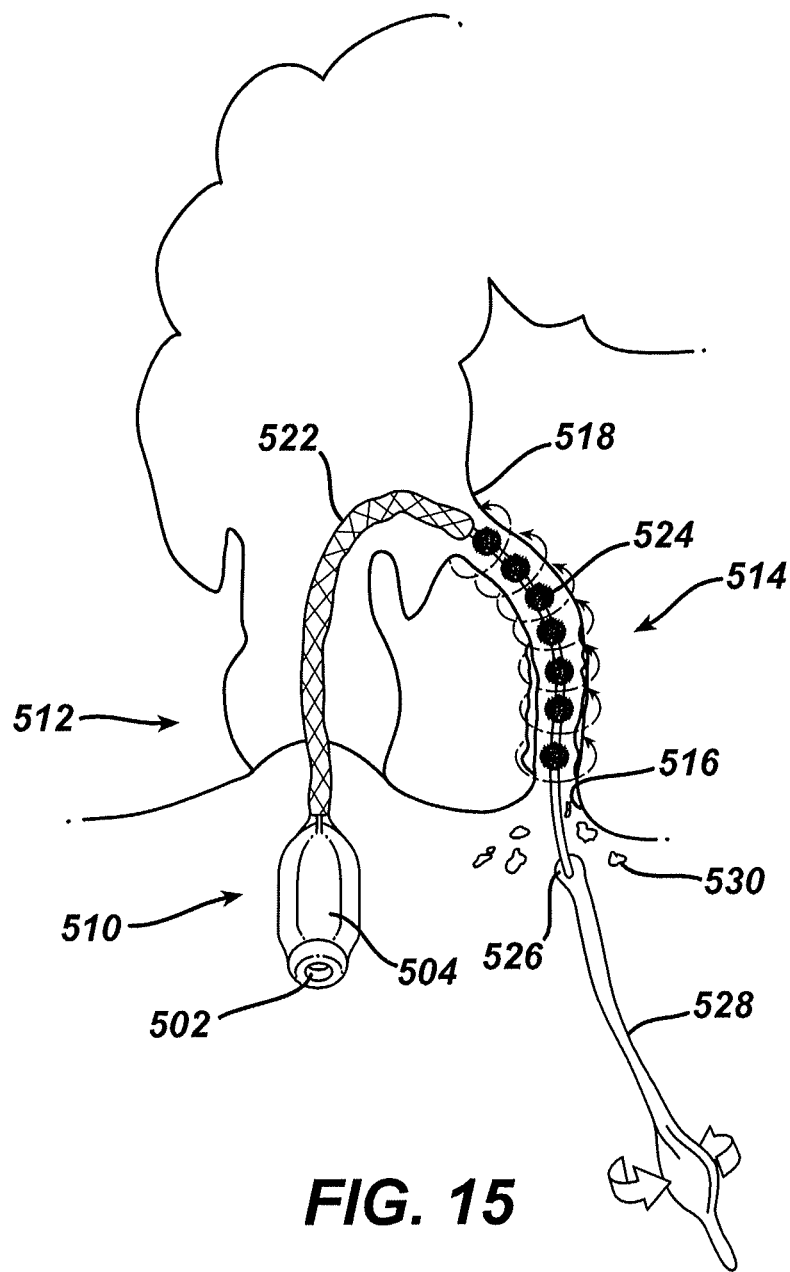
FIG. 15 depicts a perspective view of the fistula repair device of FIG. 12 being twisted within the fistula.

With threader (528) being pulled and/or pushed through fistula (514), threader (528) eventually passes through the entire length of fistula (514) and exits fistula (514). Once removed from fistula (514), the user may pull threader (528), which causes beads (524) to move through fistula (514). As beads (524) move through fistula (514), the abrasive surface of beads (524) agitates and debrides tissue from the walls of fistula (514). With a user grasping head portion (510) and threader (528), beads (524) may be reciprocated back and forth within fistula (514) in a sawing motion to facilitate the debriding process. In addition or in the alternative, a user may grasp threader (528) and twist threader (528) to rotate beads (524) within fistula (514). Such twisting may be performed while simultaneously pulling on threader (528), such that beads (524) simultaneously rotate and translate within fistula (514) as shown in FIG. 15. Of course, pulling, pushing, and twisting may be performed in any order as will be apparent to one of ordinary skill in the art in view of the teachings herein. For example, threader (528) may first be pulled, then twisted, then pulled again until fistula (514) is suitably debrided. Other suitable motions that may be used to debride fistula (514) with beads (524) will be apparent to those of ordinary skill in the art in view of the teachings herein. Debrided tissue (530) may fall out of fistula (514), may be flushed and/or suctioned from fistula (514), or may remain in fistula (514).

Figure 16:
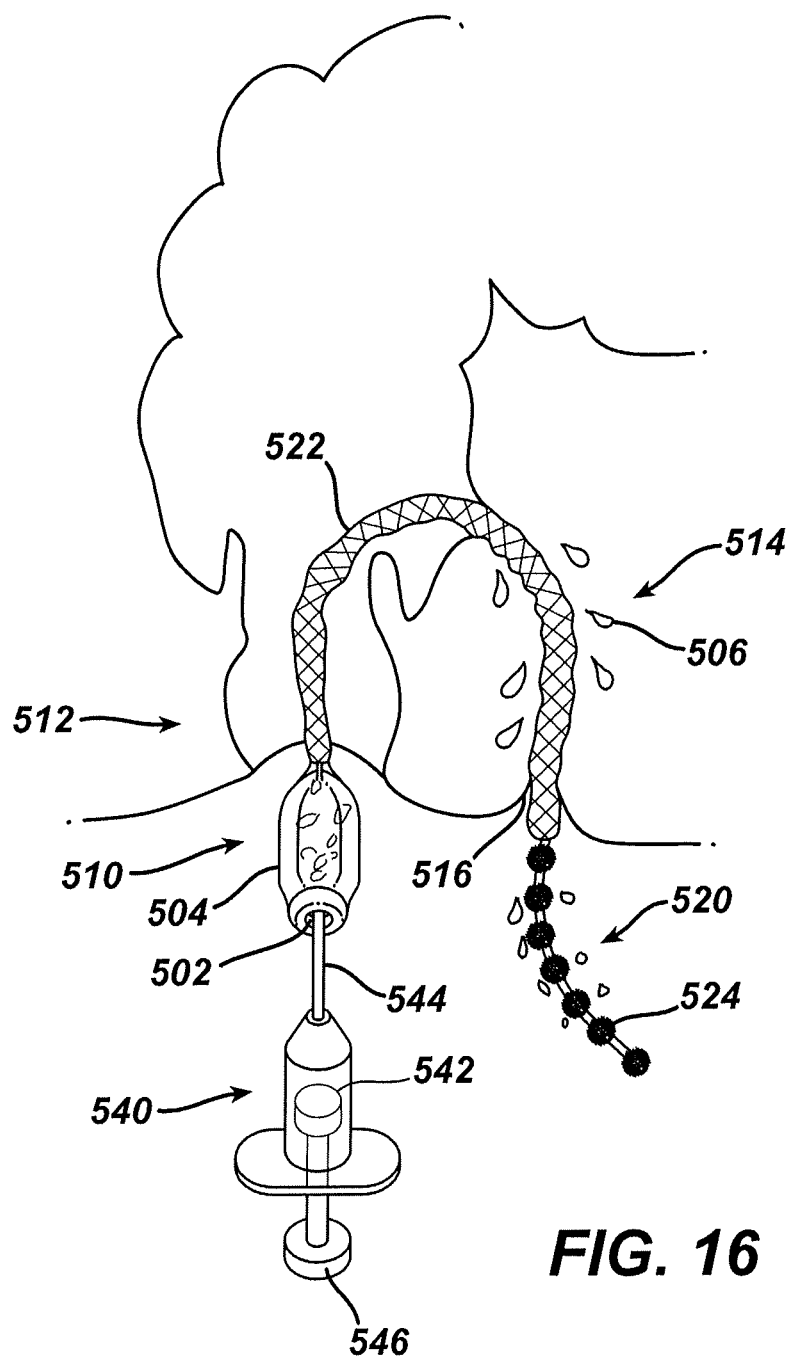
FIG. 16 depicts a perspective view of the fistula repair device of FIG. 12 being injected with a medical fluid.

Once fistula (514) has been sufficiently debrided, threader (528) is pulled further to position mesh (522) in fistula (514) as shown in FIG. 16. At this stage, cleaning chain (520) has exited fistula (514). In addition, syringe (540) is used to inject medical fluid (506) into material reservoir (504) by inserting needle (544) into injection port (502). A plunger (546) is depressed to transfer medical fluid (506) into material reservoir (502). As more medical fluid (506) is added to material reservoir (502), more medical fluid (506) is transferred to mesh (522) for delivery to fistula (514). If desired, plunger (546) may be retracted to remove medical fluid (506) from material reservoir (504). Of course, a variety of other types of devices may be used in addition to or in lieu of a syringe (504) to communicate with reservoir (504), including but not limited to a machine pump, a passive pump, or any other suitable device. In addition, mesh (522) may be pre-filled with medical fluid (506) at this stage in some versions, such that medical fluid (506) is not injected into material reservoir (502) at this stage.

Figure 17:
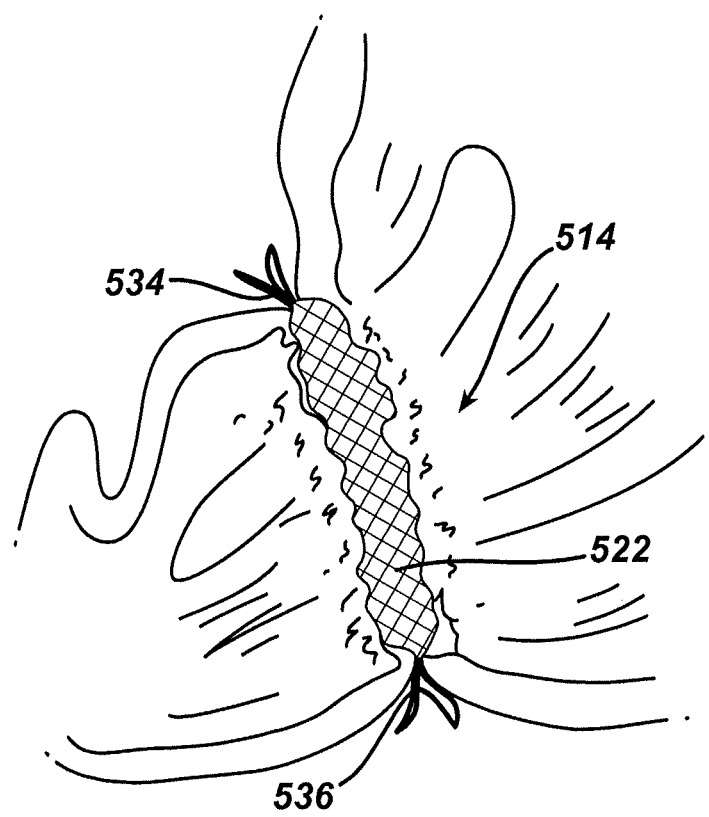
FIG. 17 depicts a side view of part of the fistula repair device of FIG. 12 positioned the fistula with the ends of the fistula sealed.

Once mesh (522) is suitably positioned and suitably filled with medical fluid (506), mesh (522) is left in fistula (514) while the rest of fistula repair device (500) is removed as shown in FIG. 17. In addition, inner opening (518) and outer opening (516) are sealed at this stage using, for example, sutures, RF sealing, or any other suitable means of sealing Inner opening (518) thus forms an inner sealed portion (534); while outer opening (516) forms an outer sealed portion (536). Inner sealed portion (534) and outer sealed portion (536) prevent mesh (522) or medical fluid (506) from escaping from fistula (514) as fistula (514) heals. If excess mesh (522) is used, the user may cut mesh (522) so as to match the length of fistula (514). Other suitable features, components, and configurations of fistula repair device (500) will be apparent to those of ordinary skill in the art in view of the teachings herein. Similarly, other suitable ways in which fistula repair device (500) may be used will be apparent to those of ordinary skill in the art in view of the teachings herein.

V. Exemplary Fistula Cleaning and Repair Device with Vacuum Port and Swab

FIGS. 18-21 shows yet another exemplary fistula repair device (600) along with an example of using fistula repair device (600). Fistula repair device (600) of this example comprises a vacuum port (610) and a catheter (604) extending through vacuum port (610). In particular, catheter (604) extends through an opening (626) in the center of vacuum port (610) created by a port door (620), and is longitudinally slidable relative to vacuum port (610). Catheter (604) comprises an insertion tip (602) having a plurality of transverse slots (628). Insertion tip (602) is rounded and blunt tip and has a diameter approximately equal to the diameter of a fistula (614). The rounded configuration of insertion tip (602) facilitates insertion into fistula (614) and further facilitates movement through fistula (614). Catheter (604) comprises a flexible material such that catheter (604) flexes to conform to the shape of fistula (614) to aid in movement through fistula (614). However any other suitable shape, dimension, or material may be used for catheter (604) as will be apparent to one of ordinary skill in the art in view of the teachings herein. Catheter slots (628) are configured to remove debrided tissue (630) as will be discussed in further detail below. In some versions, each catheter slot is defined by a sharpened edge that is configured to facilitate debriding. In addition or in the alternative, catheter (604) may include protrusions, grit, and/or any other suitable features configured to facilitate debriding.

Figure 18:
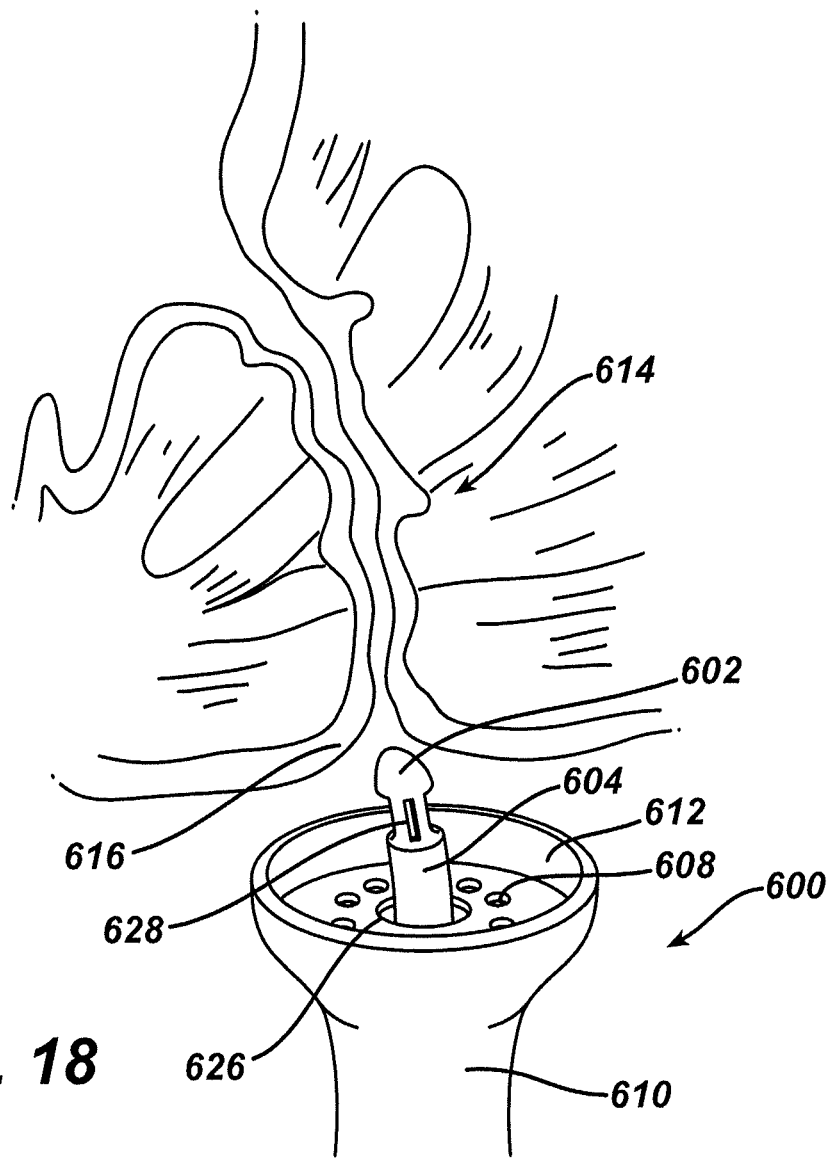
FIG. 18 depicts a perspective view of an exemplary alternative fistula repair device approaching a fistula.

Vacuum port (610) also comprises a port wall (612) and suction holes (608). Port wall (612) extends about the outer circumference of vacuum port (610) and is configured to facilitate coupling of vacuum port (610) with fistula (614). In particular, a vacuum is induced through suction holes (608) to create and substantially maintain a seal between vacuum port (610) and the tissue adjacent to outer opening (616) of fistula (614) once vacuum port (610) is engaged with outer opening (616) of fistula (614). Thus, as shown in FIG. 18, vacuum port (610) may be positioned near fistula (614) such that insertion tip (602) is positioned in front of outer opening (616) of fistula (614). In some versions, a camera or sensor may be integrated with vacuum port (610) or insertion tip (602) so as to provide for more accurate positioning of vacuum port (610).

Figure 19:
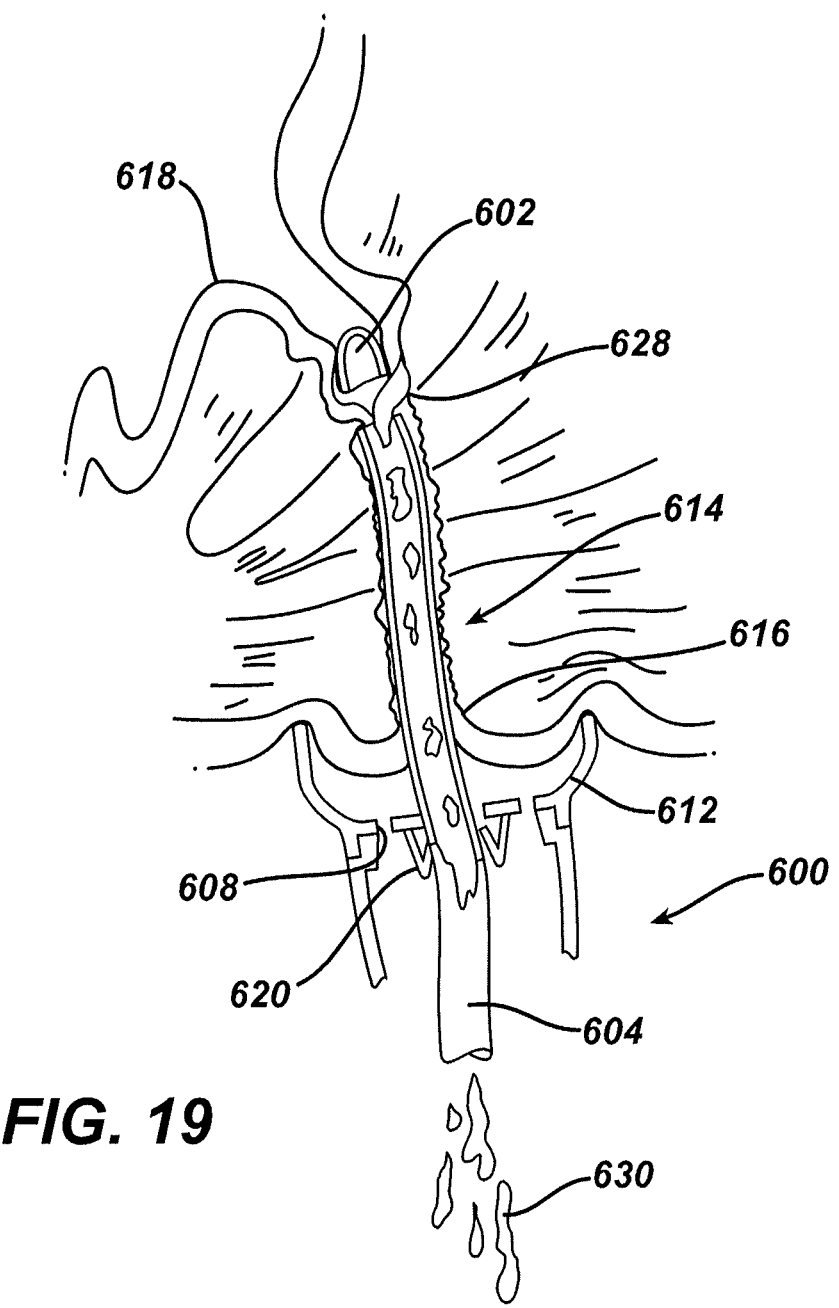
FIG. 19 depicts a side cross-sectional view of the fistula repair device of FIG. 18 engaged with the fistula.

Once vacuum port (610) has been properly positioned, insertion tip (602) is placed in fistula (614) by advancing insertion tip (602) distally relative to vacuum port (610) as shown in FIG. 19. Additionally, port wall (612) is coupled with outer opening (616) of fistula (614), which forms an air tight, substantially air tight, or liquid tight seal between port wall (612) and outer opening (616). A vacuum is applied through suction holes (608) to maintain the coupling between port wall (612) and outer opening (616). In some versions, insertion tip (602) is not advanced into fistula (614) until a substantially air tight seal is established by vacuum port (610). In the present example, catheter (604) is used to debride fistula (614). In some versions, catheter (604) is activated to apply irreversible electroporation to fistula (614), which loosens and thus debrides the wall of fistula (614). For instance, catheter (604) may include conductive portions formed by doping an insulator such as plastic with a metal oxide. In addition or in the alternative, one or more discrete metal electrodes may be built into a wall forming catheter. Other suitable ways in which electroporation may be provided by catheter (604) will be apparent to those of ordinary skill in the art in view of the teachings herein.

In addition or in the alternative, the edges defining transverse slots (628) in insertion tip (602) may be used to perform debriding. For instance, a vacuum may be applied to the interior of catheter (604), which may draw tissue that forms the wall of fistula (614) in through transverse slots (628). Catheter (604) may then be reciprocated and/or rotated within fistula (614) to sever such tissue with the edges defining transverse slots (628). Alternatively, the wall of fistula (614) may be debrided in any suitable fashion.

During or after the process of debriding, debrided tissue (630) is suctioned through catheter (604) as shown in FIG. 19. For instance, regardless of how tissue (630) is debrided, catheter (604) may be reciprocated and/or rotated within fistula (614) to suction debrided tissue (630) through transverse slots (628). Such debrided tissue (630) may be disposed of, mixed in a medical fluid, or be otherwise handled. After a sufficient amount of debrided tissue (630) is removed, catheter (604) is retracted through port door (620).

Figure 20:
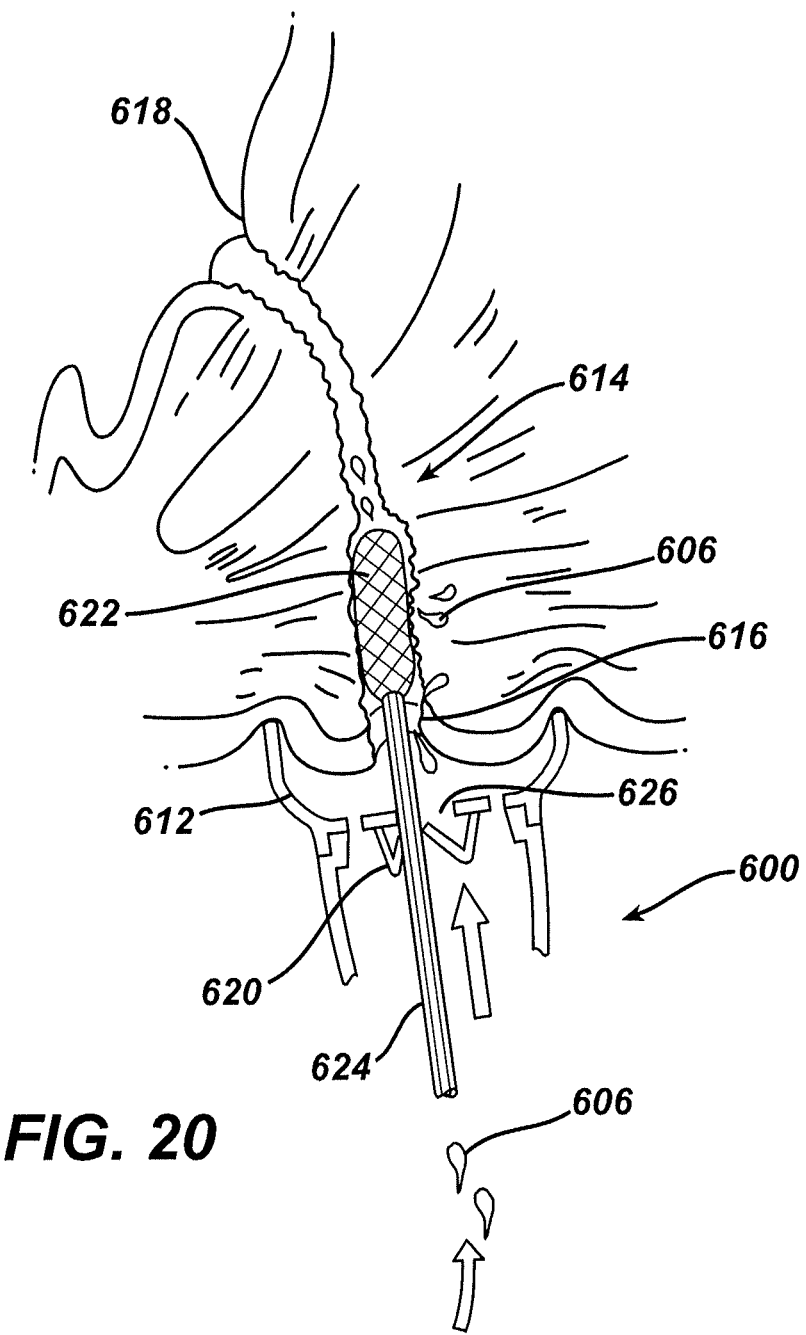
FIG. 20 depicts a side cross-sectional view of the fistula repair device of FIG. 18 with a swab inserted into the fistula.
Figure 21:
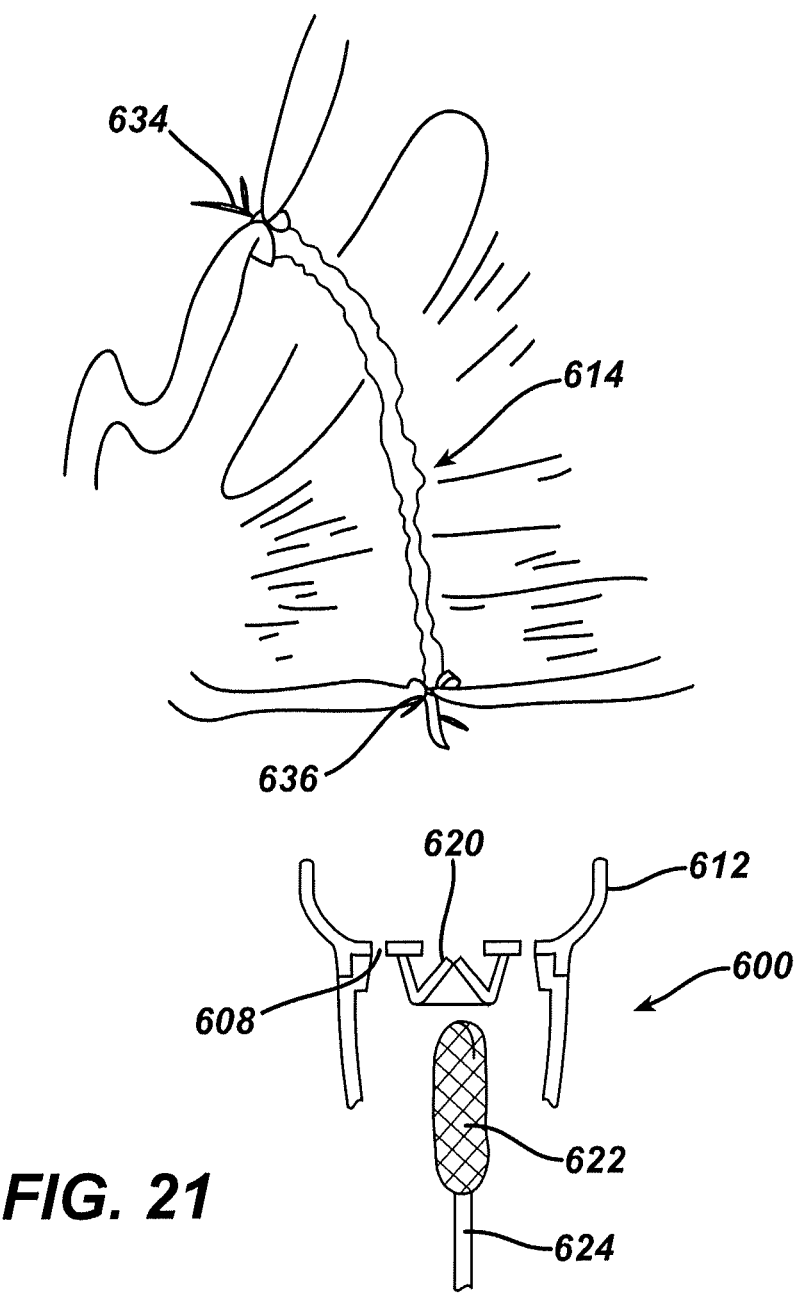
FIG. 21 depicts a side cross-sectional view of the fistula repair device of FIG. 18 separated from the fistula.

Next, a swab (622) attached to a shaft (624) is routed through port door (620) and into outer opening (616) of fistula (614) as shown in FIG. 20. Swab (622) comprises a woven material configured to hold and apply medical fluid (606). Medical fluid (606) may comprise any of the various formulations of medical fluid described herein (e.g., harvested cell tissue, a stem cell mixture, etc.). Shaft (624) is used to urge swab (622) distally through fistula (614). As swab (622) travels through the length of fistula (614), medical fluid (606) from swab (622) is applied to the wall of fistula (614). Other ways of delivering medical fluid (606) may be used, including but not limited to, an injection needle, dissolvable capsules containing medical fluid, a stent, a plug, and/or any other suitable means as will be apparent to one of ordinary skill in the art in view of the teachings herein. Once a sufficient amount of medical fluid (609) is added to fistula (614), swab (622) is removed from fistula (614) and retracted through port door (620) as shown in FIG. 21. In some versions, antibiotics are applied to fistula (614) prior to application of medical fluid (606) to fistula (614).

Once swab (622) is retracted into vacuum port (610) and is removed from fistula (614), the suction of vacuum port (610) is released so as to detach vacuum port (610) from fistula (614). Once detached from fistula (614), the ends of fistula (614) are closed using, for example, sutures, RF sealing, or any other suitable means of sealing fistula (614), which results in an outer sealed portion (636) and an inner sealed portion (634). Outer sealed portion (636) and inner sealed portion (634) are generally impermeable to fluids and generally encourage further healing of fistula (614). Other suitable features, components, and configurations of fistula repair device (600) will be apparent to those of ordinary skill in the art in view of the teachings herein. Similarly, other suitable ways in which fistula repair device (600) may be used will be apparent to those of ordinary skill in the art in view of the teachings herein.

VI. Miscellaneous

While several devices and components thereof have been discussed in detail above, it should be understood that the components, features, configurations, and methods of using the devices discussed are not limited to the contexts provided above. In particular, components, features, configurations, and methods of use described in the context of one of the devices may be incorporated into any of the other devices. Furthermore, not limited to the further description provided below, additional and alternative suitable components, features, configurations, and methods of using the devices, as well as various ways in which the teachings herein may be combined and interchanged, will be apparent to those of ordinary skill in the art in view of the teachings herein.

Versions of the devices described above may be actuated mechanically or electromechanically (e.g., using one or more electrical motors, solenoids, etc.). However, other actuation modes may be suitable as well including but not limited to pneumatic and/or hydraulic actuation, etc. Various suitable ways in which such alternative forms of actuation may be provided in a device as described above will be apparent to those of ordinary skill in the art in view of the teachings herein.

Versions of the devices described above may have various types of construction. By way of example only, any of the devices described herein, or components thereof, may be constructed from suitable metals, ceramics, plastics, or combinations thereof. Furthermore, although not required, the construction of devices described herein may be configured to be compatible with or optimize their use with various imaging technologies. For instance, a device configured for use with MRI may be constructed from all non-ferromagnetic materials. Also for instance, when using optional imaging technologies with devices described herein, certain configurations may include modifications to materials of construction such that portions or the device may readily appear in a resultant image. Various suitable ways in which these and other modifications to the construction of devices described herein may be carried out will be apparent to those of ordinary skill in the art in view of the teachings herein.

Versions of the devices described above may have application in conventional medical treatments and procedures conducted by a medical professional, as well as application in robotic-assisted medical treatments and procedures.

Versions of described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for cleaning and repairing a fistula, the apparatus comprising:
    (a) a debriding member, wherein at least a portion of the debriding member is configured to debride the walls of a fistula through contact with a wall of the fistula, wherein the debriding member defines a longitudinal axis, wherein the debriding member further comprises:
        (i) a catheter having an abrasive outer surface, and
        (ii) an anchor, wherein the anchor is located distally in relation to the catheter;
    (b) an implantable delivery member in communication with the debriding member, wherein the delivery member comprises an absorptive material configured to hold an amount of medical fluid, wherein the delivery member is configured to deliver the medical fluid to a fistula, wherein the implantable delivery member has a distal end such that the catheter is positioned between the delivery member and the anchor; and
    (c) a guide member in communication with the debriding member, wherein the guide member is configured to engage with the anchor, wherein the guide member is configured to facilitate movement of the debriding member through a fistula, wherein the guide member is located distally in relation to the debriding member along the longitudinal axis such that the debriding member is positioned between the guide member and the implantable delivery member.

2. The apparatus of claim 1, wherein the delivery member further comprises a stent, wherein the stent is configured to be positioned within a fistula to deliver medical fluid to the fistula.

3. The apparatus of claim 1, wherein the debriding member further comprises a series of linked components, wherein at least a portion of a surface of the linked components is configured to debride a wall of a fistula, wherein the linked components are arranged in an end-to-end configuration.

4. The apparatus of claim 1, wherein the delivery member further comprises a mesh material configured to receive the medical fluid, wherein the mesh material is further configured to be positioned within a portion of a fistula.

5. The apparatus of claim 1, further comprising a vacuum port, wherein the vacuum port is in communication with the debriding member, wherein the vacuum port is configured to remove loosened tissue from a fistula, wherein the vacuum port is configured to circumscribe the opening of a fistula.

6. The apparatus of claim 5, wherein the debriding member is operable to debride a fistula by electroporation.

7. The apparatus of claim 1, further comprising an actuation member operable to initiate repetitive movement of the debriding member, wherein the actuation member is further configured to be disengaged to cease repetitive movement of the debriding member.

8. The apparatus of claim 1, wherein the debriding member is configured to remove at least a portion of loose tissue from a fistula and draw the loose tissue away from the fistula.

9. An apparatus for cleaning and repairing a fistula comprising:
    (a) a guide member shaped to be drawn through a fistula;
    (b) a debriding member, wherein the guide member is operable to advance through tissue such that the debriding member trails the guide member, wherein the debriding member comprises a plurality of longitudinally aligned spherical beads, wherein each individual bead in the plurality of spherical beads has an abrasive outer surface; and (c) an implantable delivery member in communication with the debriding member, wherein the implantable delivery member is configured to hold medical fluid, wherein the implantable delivery member is operable to deliver medical fluid as the debriding member is pulled through tissue, wherein the debriding member is operable to advance through tissue such that the implantable delivery member trails the debriding member.

10. The apparatus of claim 9, wherein the implantable delivery member comprises a meshed material operable to hold a medical fluid.

11. The apparatus of claim 10, wherein the mesh material is operable to be folded while contained within the implantable delivery member.

12. The apparatus of claim 9, wherein the guide member comprises an abrasive surface.

13. The apparatus of claim 9, wherein the delivery member further comprises a stent, wherein the stent is configured to be positioned within a fistula to deliver medical fluid to the fistula.

14. The apparatus of claim 9, further comprising an actuation member operable to initiate repetitive movement of the debriding member, wherein the actuation member is further configured to be disengaged to cease repetitive movement of the debriding member.

15. The apparatus of claim 9, wherein the debriding member is configured to remove at least a portion of loose tissue from a fistula and draw the loose tissue away from the fistula.

* * * * *